United States Patent
Nagele

(10) Patent No.: US 9,746,482 B2
(45) Date of Patent: Aug. 29, 2017

(54) DIAGNOSTIC BIOMARKER PROFILES FOR THE DETECTION AND DIAGNOSIS OF PARKINSONS DISEASE

(75) Inventor: Robert G. Nagele, Turnersville, NJ (US)

(73) Assignee: Rowan University, Glassboro, NJ (US)

( * ) Notice: Subject to any disclaimer, the term of this patent is extended or adjusted under 35 U.S.C. 154(b) by 0 days.

(21) Appl. No.: 14/237,966

(22) PCT Filed: Aug. 10, 2012

(86) PCT No.: PCT/US2012/050343
§ 371 (c)(1),
(2), (4) Date: Aug. 12, 2014

(87) PCT Pub. No.: WO2013/023144
PCT Pub. Date: Feb. 14, 2013

(65) Prior Publication Data
US 2014/0364328 A1 Dec. 11, 2014

Related U.S. Application Data

(60) Provisional application No. 61/522,404, filed on Aug. 11, 2011.

(51) Int. Cl.
*C12Q 1/00* (2006.01)
*G01N 33/53* (2006.01)
*G01N 33/542* (2006.01)
*G01N 33/68* (2006.01)

(52) U.S. Cl.
CPC ..... *G01N 33/6896* (2013.01); *G01N 33/6893* (2013.01); *G01N 2800/2835* (2013.01); *G01N 2800/50* (2013.01)

(58) Field of Classification Search
None
See application file for complete search history.

(56) References Cited

U.S. PATENT DOCUMENTS

2003/0068659 A1   4/2003   Kilgannon et al.

OTHER PUBLICATIONS

Han et al., "Diagnosis of Parkinson's disease based on disease-specific autoantibody profiles in human sera.," PLoS One ePub (Feb. 22, 2012); 7(2):e32383.
Nagele et al., "Diagnosis of Alzheimer's disease based on disease-specific autoantibody profiles in human sera," PLoS One ePub Epub (Aug. 3, 2011): 6(8):e23112.
Nagele et l., "Brain reactive autoantibodies prevalent in human sera increase intraneuronal amyloid beta 1-42 deposition," J Alzheimers Dis (Apr. 2011): 25(4):605-622.
Yanamandra et al., "a-synuclein reactive antibodies as diagnositc biomarkers in blood sera of Parkinson's desiease patients," PLoS One (Apr. 25, 2011); 6(4):e18513.

*Primary Examiner* — Olga N Chernyshev
(74) *Attorney, Agent, or Firm* — Fox Rothschild LLP

(57) ABSTRACT

The present invention provides methods, compositions and kits for the detection of Parkinson' disease (PD) diagnostic biomarkers, for the diagnosis of PD, for the identification of a subject at risk for developing PD, and for the generation of patient-specific PD diagnostic biomarker profiles.

22 Claims, No Drawings

DIAGNOSTIC BIOMARKER PROFILES FOR THE DETECTION AND DIAGNOSIS OF PARKINSONS DISEASE

CROSS-REFERENCE TO RELATED APPLICATION

This application claims priority of U.S. Application Ser. No. 61/522,404 filed Aug. 11, 2011, the disclosure of which is incorporated herein by reference in its entirety.

BACKGROUND OF THE INVENTION

Parkinson's disease (PD) is a chronic and progressive motor system disorder inflicting profound social and economic costs worldwide. It is the second most common neurodegenerative disorder after Alzheimer's disease (AD), affecting more than 1% of 55-year-old individuals and more than 3% of those over the age of 75 (de Lau et al. (2006) *Lancet Neurology* 5:525-535). The primary symptoms of PD include tremor, rigidity, bradykinesia, and postural instability (Jankovic (2008) *Journal of Neurology, Neurosurgery, and Psychiatry* 79:368-376). The cardinal pathological feature of PD is the loss of dopaminergic neurons in the substantia nigra, a brain region involved in coordination and control of muscle activity (Hornykiewicz (2006) *J Neural Transm Suppl* 70:9-15). Although PD manifests primarily as a motor disability, recent studies reveal many pre-motor symptoms that suggest an onset of PD pathology years before characteristic symptoms appear. By the time a diagnosis is made, at least one-third of substantia nigra neurons and striatal dopaminergic fibers are already lost (Greffard et al. (2006) *Arch Neurol* 63:584-588).

Despite years of research, there is no one test or technique that can provide a conclusive primary diagnosis of PD. Current diagnostic methods are based on medical history evaluation and a combination of physical and neurological assessments (Hughes et al. (2002) *Brain: A Journal of Neurology* 125:861-870; Gelb et al. (1999) *Archives of Neurology* 56:33-39). Standard practices for these assessments, such as the Unified Parkinson's Disease Rating Scale (UPDRS; Goetz et al. (2008) *Movement Disorders* 23:2129-2170) have aided tremendously in clinical staging of the disease, but fail to detect PD before the onset of initial motor symptoms. Additional techniques, such as CT, MRI, and PET neuroimaging, may be used to rule out other neurological disorders, but rarely do they detect any abnormality that can be directly related to the onset of PD (Stoessl (2011) *Neurotherapeutics* 8:72-81). There are also no laboratory tests utilizing blood, cerebrospinal fluid, or urine samples that have proven to be effective in primary diagnosis or confirmation of PD.

Thus, there is a need for an accurate, relatively non-invasive, and affordable PD diagnostic test, especially one that can identify the condition at an early stage of the disease, even before significant physical symptoms are expressed. This is particularly true given widespread recognition that early detection facilitating early treatment helps to slow the progression of the disease, minimize symptoms, and improve the overall quality of life (DeKosky et al. *Science* 302:830-834).

BRIEF SUMMARY OF THE INVENTION

In one embodiment, the present invention provides a method for detecting PD diagnostic biomarkers in a subject in need of such detection comprising obtaining an immunoglobulin-containing biological sample from the subject, and performing an assay to determine the presence or absence of one or more PD diagnostic biomarkers in the biological sample.

In another embodiment, the present invention provides a method for diagnosing PD in a subject in need of such diagnosis comprising obtaining an immunoglobulin-containing biological sample from the subject, performing an assay to determine the presence or absence of one or more PD diagnostic biomarkers in the biological sample, and diagnosing PD if one or more PD diagnostic biomarkers are present.

In another embodiment, the present invention provides a method of identifying a subject at risk for developing PD comprising obtaining an immunoglobulin-containing biological sample from the subject, performing an assay to determine the presence or absence of one or more PD diagnostic biomarkers in the biological sample, and identifying the subject as at risk for developing PD if one or more of the PD diagnostic biomarkers is present.

In another embodiment, the present invention provides a method of generating a patient-specific PD diagnostic biomarker profile comprising obtaining an immunoglobulin-containing biological sample from a patient, performing an assay to determine the presence or absence of one or more PD diagnostic biomarkers in the biological sample, and generating a patient-specific PD diagnostic biomarker profile of the PD diagnostic biomarkers present in the sample.

In yet another embodiment, the present invention provides a substrate on which one or more antigens that are specific for a PD diagnostic biomarker are immobilized.

The present invention provides, in another embodiment, a microarray comprising a substrate on which one or more antigens that are specific for a PD diagnostic biomarker are immobilized.

In a further embodiment, the present invention provides a kit for detecting PD-specific antibodies.

DETAILED DESCRIPTION OF THE INVENTION

In one embodiment, the present invention provides a method for detecting PD diagnostic biomarkers in a subject in need of such detection. PD diagnostic biomarkers are defined herein as antibodies, including for example autoantibodies, that specifically bind to protein antigens and are diagnostic indicators that can be used to differentiate PD from control subjects without PD. The term "protein antigens" as used herein includes protein and peptide antigens. In one embodiment, protein antigens that have been identified as capable of being specifically bound by the PD diagnostic biomarkers are set forth in the following Table 1. The protein antigens in Table 1 are identified by art-accepted names as well as database identification numbers. The database identification numbers refer to the publically available protein databases of the National Center for Biotechnology Information (NCBI), which are well-known and accessible to those of ordinary skill in the art.

TABLE 1*

| Database ID | Description |
| --- | --- |
| NM_001544.2 | intercellular adhesion molecule 4 (Landsteiner-Wiener blood group) (ICAM4), transcript variant 1 |
| BC022098.1 | cDNA clone MGC:31944 IMAGE:4878869, complete cds |
| NM_006628.4 | cyclic AMP phosphoprotein, 19 kD (ARPP-19) |
| BC051695.1 | FERM domain containing 8 (FRMD8) |
| BC016380.1 | cDNA clone MGC:27376 IMAGE:4688477, complete cds |
| NM_032855.1 | Hematopoietic SH2 domain containing (HSH2D) |
| NM_024754.2 | pentatricopeptide repeat domain 2 (PTCD2) |
| BC015833.1 | cDNA clone MGC:27152 IMAGE:4691630, complete cds |
| BC030984.1 | cDNA clone MGC:32654 IMAGE:4701898, complete cds |
| PHR5001 | Recombinant human CTLA-4/Fc |
| BC032451.1 | cDNA clone MGC:40426 IMAGE:5178085, complete cds |
| NM_003141.2 | tripartite motif-containing 21 (TRIM21) |
| NM_002305.2 | lectin, galactoside-binding, soluble, 1 (galectin 1) (LGALS1) |
| BC094687.1 | Elongation factor 1-alpha 1 |
| NM_001167.2 | baculoviral IAP repeat-containing 4 (BIRC4) |
| NM_006790.1 | myotilin (MYOT) |
| BC030813.1 | cDNA clone MGC:22645 IMAGE:4700961, complete cds |
| BC003551.1 | transglutaminase 2 (C polypeptide, protein-glutamine-gamma-glutamyltransferase) (TGM2) |
| NM_000939.1 | proopiomelanocortin (adrenocorticotropin/beta-lipotropin/ alpha-melanocyte stimulating hormone/beta-melanocyte stimulating hormone/ beta-endorphin) (POMC), transcript variant 2 |
| NM_016207.2 | cleavage and polyadenylation specific factor 3, 73 kDa (CPSF3) |
| BC054021.1 | pterin-4 alpha-carbinolamine dehydratase/dimerization cofactor of hepatocyte nuclear factor 1 alpha (TCF1) 2 (PCBD2) |
| BC027951.1 | Cas scaffolding protein family member 4 |
| NM_002648.1 | pim-1 oncogene (PIM1) |
| BC005858.1 | fibronectin 1 (FN1) |
| BC026030.1 | zinc finger protein 239 (ZNF239) |
| NM_025104.2 | Protein DBF4 homolog B |
| BC032825.2 | SH3-domain GRB2-like 2 (SH3GL2) |
| BC019015.2 | mediator complex subunit 29 (MED29) |
| BC036723.1 | Fc fragment of IgG, low affinity IIIa, receptor (CD16a) (FCGR3A) |
| BC006423.1 | Serine/threonine-protein kinase 6 |
| BC063500.1 | Tigger transposable element-derived protein 1 |
| PHC1244 | chemokine (C-C motif) ligand 19 (CCL19) |
| BC015818.1 | lectin, galactoside-binding, soluble, 8 (galectin 8) (LGALS8) |
| NM_002307.1 | lectin, galactoside-binding, soluble, 7 (galectin 7) (LGALS7) |
| NM_021130.1 | peptidylprolyl isomerase A (cyclophilin A) (PPIA) |
| NM_024979.2 | Guanine nucleotide exchange factor DBS |
| BC022378.1 | zinc finger with KRAB and SCAN domains 1 (ZKSCAN1) |
| NM_032321.1 | hypothetical protein MGC13057 (MGC13057), transcript variant 4 |
| NM_004853.1 | syntaxin 8 (STX8) |
| BC000633.1 | Dual specificity protein kinase TTK |
| XM_378879.2 | PREDICTED: Homo sapiens hypothetical LOC400763 (LOC400763) |
| BC001935.1 | cyclin-dependent kinase inhibitor 1A (p21, Cip1) (CDKN1A) |
| NM_020168.3 | p21(CDKN1A)-activated kinase 6 (PAK6) |
| NM_003177.3 | spleen tyrosine kinase (SYK) |
| NM_003942.1 | Ribosomal protein S6 kinase alpha-4 |
| BC047722.1 | hypothetical protein MGC52110 (MGC52110) |
| NM_197972.1 | non-metastatic cells 7, protein expressed in (nucleoside-diphosphate kinase) (NME7), transcript variant 2 |
| NM_001001794.1 | family with sequence similarity 116, member B (FAM116B) |
| BC000103.1 | NCK adaptor protein 2 (NCK2) |
| NM_014321.2 | origin recognition complex, subunit 6 like (yeast) (ORC6L) |
| NM_002135.3 | nuclear receptor subfamily 4, group A, member 1 (NR4A1), transcript variant 1 |
| BC001280.1 | Serine/threonine-protein kinase 6 |
| BC000442.1 | Serine/threonine-protein kinase 12 |
| BC000896.1 | RAB10, member RAS oncogene family (RAB10) |
| BC010074.1 | FUS interacting protein (serine/arginine-rich) 1 (FUSIP1) |
| NM_207430.1 | FLJ46266 protein (FLJ46266), mRNA. |
| NM_006145.1 | DnaJ (Hsp40) homolog, subfamily B, member 1 (DNAJB1) |
| BC014928.1 | MYC-induced nuclear antigen |
| NM_012424.2 | Ribosomal protein S6 kinase delta-1 |
| BC027865.1 | chromosome 11 open reading frame 16 (C11orf16) |
| BC009108.1 | cDNA clone IMAGE:3451214 (MCM10) |
| NM_024668.2 | ankyrin repeat and KH domain containing 1 (ANKHD1), transcript variant 3 |
| NM_153750.1 | chromosome 21 open reading frame 81 (C21orf81) |
| NM_006573.2 | tumor necrosis factor (ligand) superfamily, member 13b (TNFSF13B) |
| BC000306.1 | hydroxyacyl-Coenzyme A dehydrogenase (HADH) |
| NM_005607.1 | Focal adhesion kinase 1 |
| NM_198491.1 | family with sequence similarity 92, member B (FAM92B) |
| BC056887.1 | chromosome 5 open reading frame 5 (C5orf5) |
| NM_152772.1 | T-complex protein 11-like protein 2 |
| NM_013242.1 | chromosome 16 open reading frame 80 (C16orf80) |

TABLE 1*-continued

| Database ID | Description |
| --- | --- |
| NM_014747.2 | regulating synaptic membrane exocytosis 3 (RIMS3) |
| NM_016829.1 | 8-oxoguanine DNA glycosylase (OGG1), nuclear gene encoding mitochondrial protein, transcript variant 2e |
| NM_018328.1 | methyl-CpG binding domain protein 5 (MBD5) |
| NM_003503.2 | Cell division cycle 7-related protein kinase |
| NM_002813.4 | proteasome (prosome, macropain) 26S subunit, non-ATPase, 9 (PSMD9) |
| BC006105.1 | chromosome 6 open reading frame 134 (C6orf134) |
| PV3851 | MAP/microtubule affinity-regulating kinase 4 |
| BC050718.1 | polymerase (DNA directed) kappa (POLK) |
| NM_145050.1 | coiled-coil domain containing 26 (CCDC26) |
| BC035143.1 | Tigger transposable element-derived protein 1 |
| BC036365.1 | PH domain-containing protein C10orf81 |
| BC036923.1 | chromosome 9 open reading frame 150 (C9orf150) |
| NM_016203.2 | protein kinase, AMP-activated, gamma 2 non-catalytic subunit (PRKAG2), transcript variant a, mRNA. |
| NM_152597.3 | Fibrous sheath-interacting protein 1 |
| NM_014288.2 | Centromere protein R |
| NM_003160.1 | Serine/threonine-protein kinase 13 |
| BC005332.1 | cDNA clone MGC:12418 IMAGE:3934658, complete cds |
| BC030586.2 | signal transducing adaptor molecule (SH3 domain and ITAM motif) 1 (STAM) |
| XM_086879.4 | PREDICTED: Homo sapiens hypothetical LOC150371 (LOC150371) |
| NM_175571.2 | GTPase, IMAP family member 8 (GIMAP8) |
| NM_031465.2 | chromosome 12 open reading frame 32 (C12orf32) |
| NM_053006.1 | testis-specific serine kinase 2 (TSSK2) |
| NM_014891.1 | PDGFA associated protein 1 (PDAP1) |
| NM_145174.1 | DnaJ (Hsp40) homolog, subfamily B, member 7 (DNAJB7) |
| PV3366 | v-erb-b2 erythroblastic leukemia viral oncogene homolog 2, neuro/glioblastoma derived oncogene homolog (avian) (ERBB2), transcript variant 2 |
| NM_014445.2 | stress-associated endoplasmic reticulum protein 1 (SERP1) |
| BC005807.2 | stearoyl-CoA desaturase (delta-9-desaturase) (SCD) |
| NM_003691.1 | Serine/threonine-protein kinase 16 |
| NM_017817.1 | RAB20, member RAS oncogene family (RAB20) |
| NM_004103.2 | Protein tyrosine kinase 2 beta |
| NM_177524.1 | mesoderm specific transcript homolog (mouse) (MEST), transcript variant 2 |
| NM_004832.1 | glutathione S-transferase omega 1 (GSTO1) |
| PV4803 | epidermal growth factor receptor (erythroblastic leukemia viral (v-erb-b) oncogene homolog, avian) (EGFR); see catalog number for detailed information on wild-type or point mutant status |
| NM_024033.1 | chromosome 7 open reading frame 49 (C7orf49) |
| NM_199188.1 | La ribonucleoprotein domain family, member 4 (LARP4), transcript variant 2 |
| NM_053005.2 | HCCA2 protein (HCCA2) |
| NM_012280.1 | FtsJ homolog 1 (E. coli) (FTSJ1), transcript variant 1 |
| NM_019058.1 | DNA-damage-inducible transcript 4 protein |
| NM_080659.1 | chromosome 11 open reading frame 52 (C11orf52) |
| NM_021032.2 | fibroblast growth factor 12 (FGF12), transcript variant 1 |
| NM_005340.1 | histidine triad nucleotide binding protein 1 (HINT1) |
| XM_379194.1 | PREDICTED: Homo sapiens hypothetical LOC401068 (LOC401068) |
| NM_001009880.1 | chromosome 22 open reading frame 9 (C22orf9), transcript variant 2 |
| NM_003137.2 | SFRS protein kinase 1 (SRPK1) |
| NM_003636.1 | potassium voltage-gated channel, shaker-related subfamily, beta member 2 (KCNAB2), transcript variant 1 |
| NM_005922.1 | Mitogen-activated protein kinase kinase kinase 4 |
| NM_005733.1 | kinesin family member 20A (KIF20A) |
| BC013630.1 | JTV1 gene (JTV1) |
| BC015732.1 | histidine triad nucleotide binding protein 3 (HINT3) |
| BC002950.1 | chromosome 18 open reading frame 8 (C18orf8) |
| NM_207356.1 | chromosome 1 open reading frame 174 (C1orf174) |
| NM_032352.1 | Breast cancer metastasis-suppressor 1-like protein |
| BC051762.1 | Uncharacterized protein C20orf96 |
| NM_001790.2 | cell division cycle 25 homolog C (S. pombe) (CDC25C), transcript variant 1 |
| BC047333.1 | spermatogenesis associated 9 (SPATA9) |
| BC067755.1 | potassium channel tetramerisation domain containing 18 (KCTD18) |
| BC005982.1 | peptidylprolyl isomerase A (cyclophilin A) (PPIA) |
| BC035006.2 | forty-two-three domain containing 1 (FYTTD1) |
| PV3359 | Ephrin receptor A3 (EPHA3), transcript variant 1 |
| NM_001319.5 | casein kinase 1, gamma 2 (CSNK1G2) |
| NM_172159.2 | potassium voltage-gated channel, shaker-related subfamily, beta member 1 (KCNAB1), transcript variant 3 |
| NM_003668.2 | mitogen-activated protein kinase-activated protein kinase 5 (MAPKAPK5), transcript variant 1 |
| BC033758.1 | centaurin, alpha 2 (CENTA2) |
| NM_152387.2 | BTB/POZ domain-containing protein KCTD18 |

TABLE 1*-continued

| Database ID | Description |
| --- | --- |
| BC093661.1 | Putative uncharacterized protein C14orf177 |
| NM_032138.2 | kelch repeat and BTB (POZ) domain containing 7 (KBTBD7) |
| BC066938.1 | DEAD (Asp-Glu-Ala-Asp) box polypeptide 43 (DDX43) |
| BC034435.1 | zinc finger CCCH-type containing 3 (ZC3H3) |
| BC017440.1 | trafficking protein particle complex 2-like (TRAPPC2L) |
| BC010697.1 | RNA-binding protein 40 |
| BC057767.1 | chromosome 20 open reading frame 132 (C20orf132) |
| NM_020235.2 | bobby sox homolog (*Drosophila*) (BBX) |
| BC042628.1 | serpin peptidase inhibitor, Glade E (nexin, plasminogen activator inhibitor type 1), member 2 (SERPINE2) |
| NM_017927.2 | mitofusin 1 (MFN1), nuclear gene encoding mitochondrial protein, transcript variant 2 |
| NM_002930.1 | GTP-binding protein Rit2 |
| NM_145259.1 | activin A receptor, type IC (ACVR1C) |
| NM_152376.2 | UBX domain containing 3 (UBXD3) |
| NM_017966.1 | vacuolar protein sorting 37 homolog C (*S. cerevisiae*) (VPS37C) |
| NM_016614.1 | TRAF and TNF receptor associated protein (TTRAP) |
| NM_199123.1 | SET domain containing 3 (SETD3), transcript variant 2 |
| BC002618.1 | serine/threonine kinase 16 (STK16) |
| BC043348.2 | retinitis pigmentosa 2 (X-linked recessive) (RP2) |
| NM_178002.1 | protein phosphatase 2A, regulatory subunit B' (PR 53) (PPP2R4), transcript variant 4 |
| NM_148571.1 | mitochondrial ribosomal protein L27 (MRPL27), nuclear gene encoding mitochondrial protein, transcript variant 2 |
| NM_144982.1 | coiled-coil domain containing 131 (CCDC131) |
| BC031650.1 | Putative E3 ubiquitin-protein ligase SH3RF2 |
| NM_198513.1 | PHD finger protein 20-like 1 (PHF20L1), transcript variant 3 |
| BC052995.2 | SAPS domain family, member 2 (SAPS2) |
| NM_031419.2 | NF-kappa-B inhibitor zeta |
| BC001662.1 | MAP kinase-activated protein kinase 3 |
| BC016486.1 | lectin, galactoside-binding, soluble, 8 (galectin 8) (LGALS8) |
| NM_015918.2 | processing of precursor 5, ribonuclease P/MRP subunit (*S. cerevisiae*) (POP5), transcript variant 1 |
| NM_006591.1 | polymerase (DNA-directed), delta 3, accessory subunit (POLD3) |
| NM_023931.1 | zinc finger protein 747 (ZNF747) |
| NM_152677.1 | zinc finger and SCAN domain containing 4 (ZSCAN4) |
| PV3834 | muscle, skeletal, receptor tyrosine kinase (MUSK) |
| NM_024039.1 | MIS12, MIND kinetochore complex component, homolog (yeast) (MIS12) |
| NM_022156.3 | dihydrouridine synthase 1-like (*S. cerevisiae*) (DUS1L) |
| BC062423.1 | chromosome 7 open reading frame 41 (C7orf41) |
| BC014452.1 | cDNA clone IMAGE:4903661, complete cds |
| BC039904.1 | histone deacetylase 4 (HDAC4) |
| BC020233.1 | cDNA clone MGC:31936 IMAGE:4765518, complete cds |
| NM_022491.2 | Sin3 histone deacetylase corepressor complex component SDS3 |
| NM_007255.1 | xylosylprotein beta 1,4-galactosyltransferase, polypeptide 7 (galactosyltransferase I) (B4GALT7) |
| BC013173.1 | ring finger and SPRY domain containing 1 (RSPRY1) |
| BC014924.1 | kinesin family member 2C (KIF2C) |
| NM_130848.1 | chromosome 5 open reading frame 20 (C5orf20) |
| NM_032140.1 | chromosome 16 open reading frame 48 (C16orf48) |
| NM_145702.1 | tigger transposable element derived 1 (TIGD1) |
| BC094719.1 | Rho GTPase-activating protein 12 |
| PHC0205 | interleukin 20 (IL20) |
| NM_133336.1 | Wolf-Hirschhorn syndrome candidate 1 (WHSC1), transcript variant 9 |
| BC036434.1 | Serine/threonine-protein kinase VRK2 |
| NM_003607.1 | Serine/threonine-protein kinase MRCK alpha |
| BC004207.1 | Serine/threonine-protein kinase Chk2 |
| BC010640.1 | serine/threonine kinase 3 (STE20 homolog, yeast) (STK3) |
| BC025281.1 | RNA binding motif protein 9 (RBM9) |
| NM_138558.1 | protein phosphatase 1, regulatory (inhibitor) subunit 8 (PPP1R8), transcript variant 2 |
| BC003548.1 | polymerase (DNA directed), lambda (POLL) |
| NM_002638.1 | peptidase inhibitor 3, skin-derived (SKALP) (PI3) |
| BC016486.2 | lectin, galactoside-binding, soluble, 8 (galectin 8) (LGALS8) |
| PV4879 | epidermal growth factor receptor (erythroblastic leukemia viral (v-erb-b) oncogene homolog, avian) (EGFR); see catalog number for detailed information on wild-type or point mutant status |
| NM_000115.1 | endothelin receptor type B (EDNRB), transcript variant 1 |
| BC007015.1 | cyclin E2 (CCNE2) |
| NM_182597.1 | Coiled-coil domain-containing transmembrane protein C7orf53 |
| BC064898.1 | chromosome 3 open reading frame 33 (C3orf33) |
| NM_138722.1 | BCL2-like 14 (apoptosis facilitator) (BCL2L14), transcript variant 1 |
| NM_002613.1 | 3-phosphoinositide-dependent protein kinase 1 |
| PV3757 | myosin light chain kinase 2, skeletal muscle (MYLK2) |
| NM_032858.1 | maelstrom homolog (*Drosophila*) (MAEL) |
| NM_016449.2 | hypothetical protein LOC51233 (LOC51233) |
| NM_002129.2 | high-mobility group box 2 (HMGB2) |

TABLE 1*-continued

| Database ID | Description |
|---|---|
| NM_014280.1 | DnaJ homolog subfamily C member 8 |
| NM_004939.1 | DEAD (Asp-Glu-Ala-Asp) box polypeptide 1 (DDX1) |
| NM_001001852.2 | pim-3 oncogene (PIM3) |
| BC014975.1 | family with sequence similarity 136, member A (FAM136A) |
| BC019598.1 | Zinc finger matrin-type protein 4 |
| BC048970.1 | tubulin tyrosine ligase-like family, member 7 (TTLL7) |
| BC032587.1 | tubby like protein 3 (TULP3) |
| NM_014065.2 | Protein asteroid homolog 1 |
| BC091489.1 | zinc finger, MYND domain containing 11, mRNA (cDNA clone MGC:111056 IMAGE:6186814), complete cds |
| BC057806.1 | insulin-like growth factor binding protein 1 (IGFBP1) |
| NM_016508.2 | Cyclin-dependent kinase-like 3 |
| PHC1695 | C-X-C motif chemokine 11 |
| BC010467.1 | cDNA clone MGC:17410 IMAGE:4156035, complete cds |
| BC064145.1 | CDK5 regulatory subunit associated protein 1-like 1 (CDKAL1) |
| PHC1475 | C-C motif chemokine 21 |
| NM_002904.4 | RD RNA binding protein (RDBP) |
| NM_003910.2 | BUD31 homolog (*S. cerevisiae*) (BUD31) |
| NM_133332.1 | Wolf-Hirschhorn syndrome candidate 1 (WHSC1), transcript variant 5 |
| BC000974.2 | WDR45-like (WDR45L) |
| NM_005157.2 | v-abl Abelson murine leukemia viral oncogene homolog 1 (ABL1), transcript variant a; see catalog number for detailed information on wild-type or point mutant status |
| NM_006590.2 | ubiquitin specific peptidase 39 (USP39) |
| NM_004560.2 | Tyrosine-protein kinase transmembrane receptor ROR2 |
| BC048299.1 | spermatogenesis associated, serine-rich 2 (SPATS2) |
| NM_022551.2 | ribosomal protein S18 (RPS18) |
| NM_001020.2 | ribosomal protein S16 (RPS16) |
| BC033621.2 | Pseudouridylate synthase 7 homolog-like protein |
| XM_378564.2 | PREDICTED: *Homo sapiens* hypothetical LOC400500 (LOC400500) |
| NM_000411.4 | holocarboxylase synthetase (biotin-(propriony-Coenzyme A-carboxylase (ATP-hydrolysing)) ligase) (HLCS) |
| NM_016287.2 | heterochromatin protein 1, binding protein 3 (HP1BP3) |
| NM_019067.1 | guanine nucleotide binding protein-like 3 (nucleolar)-like (GNL3L) |
| PV3873 | epidermal growth factor receptor (erythroblastic leukemia viral (v-erb-b) oncogene homolog, avian) (EGFR); see catalog number for detailed information on wild-type or point mutant status |
| BC034401.1 | cDNA clone IMAGE:5172086, partial cds |
| BC095401.1 | AKT-interacting protein |
| NM_138565.1 | cortactin (CTTN), transcript variant 2 |
| BC007401.2 | cell division cycle 25 homolog A (*S. pombe*) (CDC25A) |
| BC026346.1 | family with sequence similarity 84, member A (FAM84A) |
| XM_373800.2 | PREDICTED: *Homo sapiens* hypothetical LOC388528 (LOC388528) |
| NM_005034.2 | (polymerase (RNA) II (DNA directed) polypeptide K, 7.0 kDa POLR2K) |
| BC068514.1 | NF-kappaB repressing factor (NKRF) |
| BC047536.1 | sciellin (SCEL) |
| NM_018158.1 | solute carrier family 4 (anion exchanger), member 1, adaptor protein (SLC4A1AP) |
| NM_007373.2 | soc-2 suppressor of clear homolog (*C. elegans*) (SHOC2) |
| NM_005856.1 | receptor (G protein-coupled) activity modifying protein 3 (RAMP3) |
| NM_004088.1 | deoxynucleotidyltransferase, terminal (DNTT), transcript variant 1 |
| BC016879.1 | chromosome 6 open reading frame 113 (C6orf113) |
| NM_022063.1 | chromosome 10 open reading frame 84 (C10orf84) |
| BC011600.1 | cDNA clone IMAGE:3050953, **** WARNING: chimeric clone **** |
| NM_020397.1 | calcium/calmodulin-dependent protein kinase ID (CAMK1D), transcript variant 1 |
| XM_375456.2 | Ataxin-7-like protein 3 |
| NM_002805.1 | proteasome (prosome, macropain) 26S subunit, ATPase, 5 (PSMC5) |
| BC027617.1 | poly(A) binding protein, cytoplasmic 3 (PABPC3) |
| BC043394.1 | ankyrin repeat domain 17 (ANKRD17) |
| BC017957.1 | Protein WWC2 |
| BC001694.1 | ubiquitin-conjugating enzyme E2B (RAD6 homolog) (UBE2B) |
| NM_130897.1 | Dynein light chain roadblock-type 2 |
| NM_016167.3 | nucleolar protein 7, 27 kDa (NOL7) |
| NM_016735.1 | LIM domain kinase 1 |
| BC050563.1 | hypothetical protein LOC202051 (LOC202051) |
| NM_172014.1 | tumor necrosis factor (ligand) superfamily, member 14 (TNFSF14), transcript variant 2 |
| NM_053006.1 | testis-specific serine kinase 2 (TSSK2) |
| NM_205848.1 | synaptotagmin VI (SYT6) |
| BC010537.1 | SUB1 homolog (*S. cerevisiae*) (SUB1) |
| NM_006802.1 | splicing factor 3a, subunit 3, 60 kDa (SF3A3) |
| NM_024800.1 | Serine/threonine-protein kinase Nek11 |
| BC031821.1 | Secernin-3 |
| NM_023940.1 | RAS-like, family 11, member B (RASL11B) |
| NM_014310.3 | RASD family, member 2 (RASD2) |

TABLE 1*-continued

| Database ID | Description |
|---|---|
| XM_171154.3 | Myelin protein zero-like protein 1 |
| BC062696.1 | microsomal triglyceride transfer protein (MTTP) |
| BC016842.1 | LSM14A, SCD6 homolog A (*S. cerevisiae*) (LSM14A) |
| NM_022347.1 | interferon responsive gene 15 (IFRG15) |
| NM_018063.3 | helicase, lymphoid-specific (HELLS) |
| NM_003868.1 | fibroblast growth factor 16 (FGF16) |
| PV3870 | discoidin domain receptor family, member 2 (DDR2), transcript variant 1 |
| BC095406.1 | Core histone macro-H2A.1 |
| NM_001880.2 | activating transcription factor 2 (ATF2) |
| BC001755.1 | Leiomodin-1 |
| BC012289.1 | KIAA0515 (KIAA0515) |
| BC000770.1 | death inducer-obliterator 1 (DIDO1) |
| BC016276.1 | Disks large-associated protein 5 |
| NM_003948.2 | Cyclin-dependent kinase-like 2 |
| BC032851.2 | Cas-Br-M (murine) ecotropic retroviral transforming sequence b (CBLB) |
| BC011454.1 | angiomotin like 2 (AMOTL2) |
| NM_015920.3 | 40S ribosomal protein S27-like protein |
| BC000468.1 | ubiquitin-conjugating enzyme E2 variant 1 (UBE2V1) |
| NM_013323.1 | sorting nexin 11 (SNX11), transcript variant 2 |
| NM_005825.2 | RAS guanyl releasing protein 2 (calcium and DAG-regulated) (RASGRP2), transcript variant 1 |
| NM_032023.3 | Ras association (RalGDS/AF-6) domain family 4 (RASSF4) |
| NM_006223.1 | protein (peptidylprolyl cis/trans isomerase) NIMA-interacting, 4 (parvulin) (PIN4) |
| BC041099.1 | nudix (nucleoside diphosphate linked moiety X)-type motif 12 (NUDT12) |
| NM_022839.2 | mitochondrial ribosomal protein S11 (MRPS11), nuclear gene encoding mitochondrial protein, transcript variant 1 |
| NM_199190.1 | La ribonucleoprotein domain family, member 4 (LARP4), transcript variant 3 |
| NM_153043.3 | hypothetical protein FLJ37078 (FLJ37078) |
| NM_024588.2 | hypothetical protein FLJ23584 (FLJ23584) |
| NM_001008737.1 | hypothetical LOC401052 (LOC401052) |
| NM_001396.2 | Dual specificity tyrosine-phosphorylation-regulated kinase 1A |
| NM_004935.1 | cyclin-dependent kinase 5 (CDK5) and p25: CDK5 and p25 sequences are seperated by -- (in protein list file). |
| BC031549.1 | CDC-like kinase 1 (CLK1) |
| NM_014570.2 | ADP-ribosylation factor GTPase activating protein 3 (ARFGAP3) |
| NM_016505.2 | zinc finger, CCHC domain containing 17 (ZCCHC17) |
| BC015738.1 | Zinc finger FYVE domain-containing protein 19 |
| NM_002822.3 | twinfilin, actin-binding protein, homolog 1 (*Drosophila*) (TWF1) |
| NM_153345.1 | transmembrane protein 139 (TMEM139) |
| NM_005901.2 | SMAD family member 2 (SMAD2), transcript variant 1 |
| NM_004349.2 | runt-related transcription factor 1; translocated to, 1 (cyclin D-related) (RUNX1T1), transcript variant 1 |
| NM_001014.2 | ribosomal protein S10 (RPS10) |
| BC033710.2 | RAD54 homolog B (*S. cerevisiae*) (RAD54B) |
| XM_378988.2 | PREDICTED: Homo sapiens hypothetical LOC400849 (LOC400849) |
| NM_002608.1 | platelet-derived growth factor beta polypeptide (simian sarcoma viral (v-sis) oncogene homolog) (PDGFB), transcript variant 1 |
| BC012381.1 | Neuropilin and tolloid-like protein 2 |
| BC033035.1 | hypothetical locus FLJ25758 (FLJ25758) |
| NM_004493.1 | hydroxysteroid (17-beta) dehydrogenase 10 (HSD17B10), nuclear gene encoding mitochondrial protein, transcript variant 1 |
| NM_017856.1 | gem (nuclear organelle) associated protein 8 (GEMIN8), transcript variant 3 |
| NM_000799.2 | erythropoietin (EPO) |
| BC047056.1 | DnaJ (Hsp40) homolog, subfamily B, member 2 (DNAJB2) |
| BC056669.1 | DCN1, defective in cullin neddylation 1, domain containing 2 (*S. cerevisiae*) (DCUN1D2) |
| BC020647.1 | coiled-coil domain containing 59 (CCDC59) |
| BC017570.1 | chromosome 9 open reading frame 78 (C9orf78) |
| NM_016520.1 | chromosome 9 open reading frame 78 (C9orf78) |
| NM_003503.2 | Cell division cycle 7-related protein kinase |
| BC000784.1 | baculoviral IAP repeat-containing 5 (survivin) (BIRC5) |
| NM_021709.1 | Apoptosis regulatory protein Siva |
| BC096708.1 | Wilms tumor-associated protein |
| BC018060.1 | Ras-like without CAAX 2 (RIT2) |
| NM_006912.3 | Ras-like without CAAX 1 (RIT1) |
| NM_012387.1 | peptidyl arginine deiminase, type IV (PADI4) |
| NM_018039.2 | jumonji domain containing 2D (JMJD2D) |
| BC015202.2 | centromere protein T (CENPT) |
| NM_145008.1 | Protein yippee-like 4 |
| NM_007079.2 | Protein tyrosine phosphatase type IVA 3 |
| NM_003688.1 | Peripheral plasma membrane protein CASK |

TABLE 1*-continued

| Database ID | Description |
|---|---|
| NM_139355.1 | megakaryocyte-associated tyrosine kinase (MATK), transcript variant 1 |
| NM_002309.2 | leukemia inhibitory factor (cholinergic differentiation factor) (LIF) |
| NM_001950.3 | E2F transcription factor 4, p107/p130-binding (E2F4) |
| NM_018956.2 | chromosome 9 open reading frame 9 (C9orf9) |
| NM_080862.1 | SPRY domain-containing SOCS box protein 4 |
| NM_014790.3 | janus kinase and microtubule interacting protein 2 (JAKMIP2) |
| NM_198219.1 | Inhibitor of growth protein 1 |
| NM_003831.1 | RIO kinase 3 (yeast) (RIOK3) |
| NM_002945.2 | replication protein A1, 70 kDa (RPA1) |
| BC014789.1 | UDP-N-acetyl-alpha-D-galactosamine:polypeptide N-acetylgalactosaminyltransferase-like 2 (GALNTL2) |
| NM_138551.1 | thymic stromal lymphopoietin (TSLP), transcript variant 2 |
| NM_145242.1 | similar to POSSIBLE GUSTATORY RECEPTOR CLONE PTE01 (LOC115131) |
| NM_001011538.1 | similar to 60S ribosomal protein L21 (LOC402176) |
| NM_002576.2 | Serine/threonine-protein kinase PAK 1 |
| NM_005620.1 | S100 calcium binding protein A11 (S100A11) |
| NM_005669.3 | Receptor expression-enhancing protein 5 |
| NM_002870.1 | RAB13, member RAS oncogene family (RAB13) |
| NM_152757.1 | Putative uncharacterized protein C20orf200 |
| NM_002652.1 | prolactin-induced protein (PIP) |
| NM_152329.3 | Peptidylprolyl isomerase-like 5 |
| NM_014431.1 | Paladin |
| NM_024578.1 | occludin/ELL domain containing 1 (OCEL1) |
| NM_173796.2 | hypothetical protein MGC24125 (MGC24125) |
| BC011842.2 | hypothetical protein FLJ11184 (FLJ11184) |
| BC013352.1 | HpaII tiny fragments locus 9c protein |
| NM_006620.2 | HBS1-like (*S. cerevisiae*) (HBS1L) |
| NM_004286.2 | GTP binding protein 1 (GTPBP1) |
| BC053866.1 | endothelin 3 (EDN3) |
| NM_001005266.1 | Dresden prostate carcinoma protein 2 |
| NM_057749.1 | cyclin E2 (CCNE2) |
| NM_006438.2 | Collectin-10 |
| NM_017785.2 | coiled-coil domain containing 99 (CCDC99) |
| NM_152353.1 | claudin domain containing 2 (CLDND2) |
| NM_207337.1 | antagonist of mitotic exit network 1 homolog (*S. cerevisiae*) (AMN1) |
| BC011399.1 | spleen tyrosine kinase (SYK) |
| BC040106.1 | hypothetical protein HSPC111 (HSPC111) |
| NM_197962.1 | glutaredoxin 2 (GLRX2), transcript variant 2 |
| BC006318.1 | erythrocyte membrane protein band 4.9 (dematin) (EPB49) |
| NM_145010.1 | chromosome 10 open reading frame 63 (C10orf63) |
| NM_199139.1 | XIAP associated factor-1 (XAF1), transcript variant 2 |
| NM_172160.1 | potassium voltage-gated channel, shaker-related subfamily, beta member 1 (KCNAB1), transcript variant 1 |
| NM_017772.2 | TBC1 domain family member 22B |
| NM_020317.2 | chromosome 1 open reading frame 63 (C1orf63) |
| BC004236.2 | ubiquitin-conjugating enzyme E2S (UBE2S) |
| NM_007172.2 | nucleoporin 50 kDa (NUP50), transcript variant 2 |
| NM_145909.1 | Zinc finger protein 323 |
| NM_003295.1 | tumor protein, translationally-controlled 1 (TPT1) |
| BC008042.2 | Tumor necrosis factor ligand superfamily member 13 |
| BC059174.1 | TRAF3-interacting protein 1 |
| NM_004755.1 | Ribosomal protein S6 kinase alpha-5 |
| BC038509.1 | regulator of calcineurin 2 (DSCR1L1) |
| NM_198829.1 | Ras-related C3 botulinum toxin substrate 1 |
| BC033748.1 | pyridoxal-dependent decarboxylase domain containing 1 (PDXDC1) |
| XM_379430.1 | PREDICTED: *Homo sapiens* hypothetical protein LOC285758 (LOC285758) |
| BC017114.1 | oligonucleotide/oligosaccharide-binding fold containing 2A (OBFC2A) |
| NM_017838.2 | nucleolar protein family A, member 2 (H/ACA small nucleolar RNPs) (NOLA2), transcript variant 1 |
| NM_133494.1 | NIMA (never in mitosis gene a)-related kinase 7 (NEK7) |
| NM_006303.2 | NA |
| Histone-type IIA | JTV1 gene (JTV1) |
| BC001327.1 | interferon-related developmental regulator 2 (IFRD2) |
| NM_201516.1 | H2A histone family, member V (H2AFV), transcript variant 4 |
| BC020803.1 | developmentally regulated GTP binding protein 1 (DRG1) |
| NM_020139.1 | 3-hydroxybutyrate dehydrogenase, type 2 (BDH2) |
| NM_021967.1 | small EDRK-rich factor 1A (telomeric) (SERF1A) |
| NM_182970.2 | regulating synaptic membrane exocytosis 4 (RIMS4) |
| NM_001040633.1 | protein kinase, AMP-activated, gamma 2 non-catalytic subunit (PRKAG2), transcript variant c, mRNA |
| BC036089.1 | myeloid/lymphoid or mixed-lineage leukemia (trithorax homolog, *Drosophila*); translocated to, 3 (MLLT3) |
| NM_018439.1 | Impact homolog (mouse) (IMPACT) |
| BC005043.1 | hypothetical protein MGC31957 (MGC31957) |

TABLE 1*-continued

| Database ID | Description |
| --- | --- |
| NM_033642.1 | fibroblast growth factor 13 (FGF13), transcript variant 1B |
| NM_032377.2 | elongation factor 1 homolog (*S. cerevisiae*) (ELOF1) |
| BC053656.1 | EGF-like repeats and discoidin I-like domains 3 (EDIL3) |
| NM_006252.2 | AMP-activated protein_kinase A2/B1/G1: PRKAA2/B1/G1 sequences are seperated by -- (in protein list file). |
| BC002559.1 | YTH domain family, member 2 (YTHDF2) |
| BC095404.1 | Protein transport protein Sec23B |
| NM_152377.1 | chromosome 1 open reading frame 87 (C1orf87) |
| NM_001004306.1 | similar to hypothetical protein FLJ36492 (MGC87631) |
| BC011781.2 | chromosome 9 open reading frame 37 (C9orf37) |
| NM_145691.3 | ATP synthase mitochondrial F1 complex assembly factor 2 (ATPAF2), nuclear gene encoding mitochondrial protein |
| BC040183.2 | Rap guanine nucleotide exchange factor (GEF) 4 (RAPGEF4) |
| NM_002540.3 | outer dense fiber of sperm tails 2 (ODF2), transcript variant 1 |
| NM_003384.1 | *vaccinia* related kinase 1 (VRK1) |
| BC036184.1 | Tropomodulin-2 |
| BC002637.1 | Tribbles homolog 2 |
| NM_004226.1 | Serine/threonine-protein kinase 17B |
| BC007411.2 | Protein diaphanous homolog 1 |
| NM_002677.1 | peripheral myelin protein 2 (PMP2) |
| PV3293 | mitogen-activated protein kinase kinase 6 (MAP2K6), transcript variant 2; see catalog number for detailed information on wild-type or point mutant status |
| BC098302.1 | Kanadaptin |
| NM_145899.1 | high mobility group AT-hook 1 (HMGA1), transcript variant 1 |
| BC063275.1 | eukaryotic translation initiation factor 2C, 1 (EIF2C1) |
| NM_004060.2 | cyclin G1 (CCNG1), transcript variant 1 |
| BC051031.1 | chromosome 11 open reading frame 74 (C11orf74) |
| NM_018120.3 | armadillo repeat containing 1 (ARMC1) |
| PV3867 | anaplastic lymphoma kinase (Ki-1) (ALK) |
| BC064984.1 | additional sex combs like 1 (*Drosophila*) (ASXL1) |
| NM_153645.1 | nucleoporin 50 kDa (NUP50), transcript variant 3 |
| BC003065.1 | Cell division protein kinase 2 |
| BC065928.1 | ubiquitin specific peptidase 28 (USP28) |
| NM_013233.1 | STE20/SPS1-related proline-alanine-rich protein kinase |
| BC057783.1 | splicing factor, arginine/serine-rich 2B (SFRS2B) |
| NM_006800.2 | male-specific lethal 3-like 1 (*Drosophila*) (MSL3L1), transcript variant 3 |
| BC000758.1 | Coiled-coil domain-containing protein 28A |
| BC050645.1 | bystin-like (BYSL) |
| BC006083.1 | tyrosyl-DNA phosphodiesterase 1 (TDP1) |
| NM_005884.2 | p21(CDKN1A)-activated kinase 4 (PAK4), transcript variant 1 |
| BC042608.1 | family with sequence similarity 90, member A1 (FAM90A1) |
| BC013366.2 | UNC-112 related protein 2 (URP2) |
| BC047945.1 | tripartite motif-containing 69 (TRIM69) |
| BC010929.1 | LIM domain binding 3 (LDB3) |
| NM_020961.2 | KIAA1627 protein (KIAA1627) |
| NM_031473.1 | Intraflagellar transport protein 81 homolog |
| NM_018010.2 | intraflagellar transport 57 homolog (*Chlamydomonas*) (IFT57) |
| NM_139016.2 | chromosome 20 open reading frame 198 (C20orf198) |
| BC060814.1 | centaurin, gamma 2 (CENTG2) |
| NM_152243.1 | Cdc42 effector protein 1 |
| BC020972.1 | Casein kinase I isoform gamma-2 |
| NM_017451.1 | BAI1-associated protein 2 (BAIAP2), transcript variant 2 |
| NM_000989.2 | ribosomal protein L30 (RPL30) |
| NM_006498.1 | lectin, galactoside-binding, soluble, 2 (LGALS2) |
| BC015586.2 | laminin, gamma 1 (formerly LAMB2) (LAMC1) |
| NM_145315.2 | lactation elevated 1 (LACE1) |
| NM_001008572.1 | tubulin tyrosine ligase-like family, member 1 (TTLL1), transcript variant 2 |
| NM_153764.1 | potassium inwardly-rectifying channel, subfamily J, member 1 (KCNJ1), transcript variant rom-k2 |
| NM_017588.1 | WD repeat domain 5 (WDR5), transcript variant 1 |
| BC011526.1 | PCTAIRE protein kinase 3 (PCTK3) |
| NM_004507.1 | HUS1 checkpoint homolog (*S. pombe*) (HUS1) |
| NM_032359.1 | chromosome 3 open reading frame 26 (C3orf26) |
| BC001553.1 | chromatin modifying protein 2B (CHMP2B) |
| NM_001896.2 | casein kinase 2, alpha prime polypeptide (CSNK2A2) |
| BC017328.2 | angiotensin II receptor-associated protein (AGTRAP) |
| BC014271.2 | endoglin (Osler-Rendu-Weber syndrome 1) (ENG) |
| NM_013313.3 | yippee-like 1 (*Drosophila*) (YPEL1) |
| BC010919.1 | ribosomal protein L35 (RPL35) |
| BC018929.1 | pleckstrin homology-like domain, family A, member 1 (PHLDA1) |
| NM_032728.2 | phosphatidic acid phosphatase type 2 domain containing 3 (PPAPDC3) |
| BC059947.1 | chondrosarcoma associated gene 1 (CSAG1) |
| NM_001274.2 | CHK1 checkpoint homolog (*S. pombe*) (CHEK1) |
| BC001780.1 | Uncharacterized methyltransferase WBSCR22 |

TABLE 1*-continued

| Database ID | Description |
|---|---|
| NM_054035.1 | unc-119 homolog (*C. elegans*) (UNC119), transcript variant 2 |
| NM_201263.1 | tryptophanyl tRNA synthetase 2, mitochondrial (WARS2), nuclear gene encoding mitochondrial protein, transcript variant 2 |
| NM_013293.1 | Transformer-2 protein homolog |
| BC035573.1 | transcription elongation factor A (SII)-like 8 (TCEAL8) |
| NM_001003799.1 | TCR gamma alternate reading frame protein (TARP), nuclear gene encoding mitochondrial protein, transcript variant 1 |
| NM_006306.2 | structural maintenance of chromosomes 1A (SMC1A) |
| NM_003930.2 | src kinase associated phosphoprotein 2 (SKAP2) |
| BC032382.1 | similar to pleckstrin homology domain containing, family M (with RUN domain) member 1; adapter protein 162, mRNA, complete cds. |
| NM_017886.1 | Serine/threonine-protein kinase ULK4 |
| NM_018650.1 | Serine/threonine-protein kinase MARK1 |
| NM_003576.2 | Serine/threonine-protein kinase 24 |
| NM_000987.2 | ribosomal protein L26 (RPL26) |
| BC052303.1 | Rho GTPase activating protein 4 (ARHGAP4) |
| BC004349.1 | RAN binding protein 3 (RANBP3) |
| NM_133341.1 | RAD17 homolog (*S. pombe*) (RAD17), transcript variant 4 |
| BC070073.1 | Protein ZNF365 |
| XM_374177.2 | PREDICTED: *Homo sapiens* hypothetical LOC389415 (LOC389415) |
| BC009046.1 | neurogenic differentiation 1 (NEUROD1) |
| NM_145043.1 | nei like 2 (*E. coli*) (NEIL2) |
| NM_016497.2 | mitochondrial ribosomal protein L51 (MRPL51), nuclear gene encoding mitochondrial protein |
| NM_002402.1 | mesoderm specific transcript homolog (mouse) (MEST), transcript variant 1 |
| NM_032853.2 | melanoma associated antigen (mutated) 1 (MUM1) |
| BC017168.1 | leucine rich repeat containing 59 (LRRC59) |
| NM_003724.1 | jerky homolog (mouse) (JRK), transcript variant 1 |
| NM_175065.2 | histone cluster 2, H2ab (HIST2H2AB) |
| NM_005307.1 | G protein-coupled receptor kinase 4 |
| BC004884.2 | fucosyltransferase 10 (alpha (1,3) fucosyltransferase) (FUT10) |
| NM_003677.3 | Density-regulated protein |
| NM_021117.1 | Cryptochrome 2 (photolyase-like) (CRY2) |
| NM_024563.1 | chromosome 5 open reading frame 23 (C5orf23) |
| NM_032338.2 | chromosome 12 open reading frame 31 (C12orf31) |
| NM_006072.4 | chemokine (C-C motif) ligand 26 (CCL26) |
| BC056401.1 | centaurin, delta 2 (CENTD2) |
| NM_017593.2 | BMP-2-inducible protein kinase |
| NM_015833.1 | adenosine deaminase, RNA-specific, B1 (RED1 homolog rat) (ADARB1), transcript variant 2 |
| NM_022756.2 | Uncharacterized protein C1orf149 |
| NM_006439.3 | Protein mab-21-like 2 |
| BC001370.2 | LIM and senescent cell antigen-like domains 2 (LIMS2) |
| NM_058229.2 | F-box protein 32 (FBXO32), transcript variant 1 |
| NM_018199.1 | exonuclease 3'-5' domain-like 2 (EXDL2) |
| NM_012148.1 | double homeobox, 3 (DUX3) |
| BC011924.1 | unkempt homolog (*Drosophila*)-like (UNKL) |
| BC009010.1 | Uncharacterized protein C6orf142 homolog |
| NM_181838.1 | Ubiquitin-conjugating enzyme E2 D2 |
| NM_152876.1 | Tumor necrosis factor receptor superfamily member 6 |
| NM_000594.2 | tumor necrosis factor (TNF superfamily, member 2) (TNF); see catalog number for detailed information on wild-type or point mutant status |
| BC048969.1 | TSPY-like 1 (TSPYL1) |
| NM_003289.3 | tropomyosin 2 (beta) (TPM2), transcript variant 1 |
| NM_021158.1 | tribbles homolog 3 (*Drosophila*) (TRIB3) |
| NM_004178.3 | TAR (HIV-1) RNA binding protein 2 (TARBP2), transcript variant 3 |
| NM_015978.1 | Serine/threonine-protein kinase TNNI3K |
| BC068537.1 | serine palmitoyltransferase, long chain base subunit 1 (SPTLC1) |
| NM_174903.2 | RING finger protein 151 |
| NM_001029.2 | ribosomal protein S26 (RPS26) |
| NM_018111.1 | Putative uncharacterized protein FLJ10490 |
| BC007424.2 | PRP4 pre-mRNA processing factor 4 homolog (yeast) (PRPF4) |
| NM_006254.3 | protein kinase C, delta (PRKCD), transcript variant 1 |
| BC019268.1 | Protein arginine N-methyltransferase 1 |
| XM_294794.1 | PREDICTED: *Homo sapiens* similar to putative membrane-bound dipeptidase 2 (LOC339065) |
| XM_374026.1 | PREDICTED: *Homo sapiens* hypothetical LOC389081 (LOC389081) |
| XM_084990.6 | PREDICTED: *Homo sapiens* hypothetical LOC144962 (LOC144962) |
| NM_174930.2 | postmeiotic segregation increased 2-like 5 (PMS2L5) |
| NM_001722.2 | polymerase (RNA) III (DNA directed) polypeptide D, 44 kDa (POLR3D) |
| NM_006607.1 | pituitary tumor-transforming 2 (PTTG2) |
| NM_024928.3 | oligonucleotide/oligosaccharide-binding fold containing 1 (OBFC1) |
| NM_014582.1 | odorant binding protein 2A (OBP2A) |
| BC024919.1 | nucleotide binding protein-like (NUBPL) |
| BC032598.1 | NHL repeat containing 2 (NHLRC2) |

TABLE 1*-continued

| Database ID | Description |
|---|---|
| BC001715.2 | NADH dehydrogenase (ubiquinone) Fe-S protein 7, 20 kDa (NADH-coenzyme Q reductase) (NDUFS7) |
| NM_014763.2 | mitochondrial ribosomal protein L19 (MRPL19), nuclear gene encoding mitochondrial protein |
| NM_002391.1 | midkine (neurite growth-promoting factor 2) (MDK), transcript variant 3 |
| BC002755.1 | MAP kinase-interacting serine/threonine-protein kinase 1 |
| BC003164.1 | leukocyte receptor cluster (LRC) member 4 (LENG4) |
| PHC0045 | interleukin 4 (IL4), transcript variant 1 |
| NM_175923.2 | hypothetical protein MGC42630 (MGC42630) |
| NM_001002018.1 | host cell factor C1 regulator 1 (XPO1 dependent) (HCFC1R1), transcript variant 3 |
| NM_178425.1 | histone deacetylase 9 (HDAC9), transcript variant 5 |
| NM_003517.2 | histone cluster 2, H2ac (HIST2H2AC) |
| NM_032124.3 | haloacid dehalogenase-like hydrolase domain containing 2 (HDHD2) |
| NM_005324.3 | H3 histone, family 3B (H3.3B) (H3F3B) |
| NM_002093.2 | glycogen synthase kinase 3 beta (GSK3B) |
| NM_003996.2 | glutathione peroxidase 5 (epididymal androgen-related protein) (GPX5), transcript variant 2, mRNA. |
| NM_000800.2 | fibroblast growth factor 1 (acidic) (FGF1), transcript variant 1 |
| BC000733.1 | eukaryotic translation initiation factor 3, subunit G (EIF3S4) |
| PV3872 | epidermal growth factor receptor (erythroblastic leukemia viral (v-erb-b) oncogene homolog, avian) (EGFR); see catalog number for detailed information on wild-type or point mutant status |
| NM_152991.1 | embryonic ectoderm development (EED), transcript variant 2 |
| BC013648.1 | EF-hand domain family, member D2 (EFHD2) |
| BC012021.1 | E3 ubiquitin-protein ligase RNF125 |
| NM_006482.1 | Dual specificity tyrosine-phosphorylation-regulated kinase 2 |
| NM_004071.1 | Dual specificity protein kinase CLK1 |
| NM_003935.3 | DNA topoisomerase 3-beta-1 |
| NM_004728.2 | DEAD (Asp-Glu-Ala-Asp) box polypeptide 21 (DDX21) |
| NM_001311.2 | Cysteine-rich protein 1 |
| BC009348.2 | cirrhosis, autosomal recessive 1A (cirhin) (CIRH1A) |
| BC062359.1 | chromosome 8 open reading frame 47 (C8orf47) |
| BC003595.1 | chromosome 17 open reading frame 62 (C17orf62) |
| BC013900.1 | chromosome 12 open reading frame 41 (C12orf41) |
| NM_016507.1 | Cell division cycle 2-related protein kinase 7 |
| NM_139062.1 | casein kinase 1, delta (CSNK1D), transcript variant 2 |
| NM_138559.1 | B-cell CLL/lymphoma 11A (zinc finger protein) (BCL11A), transcript variant 3 |
| NM_015850.2 | Basic fibroblast growth factor receptor 1 |
| NM_004217.1 | aurora kinase B (AURKB) |
| NM_172028.1 | ankyrin repeat and BTB (POZ) domain containing 1 (ABTB1), transcript variant 3 |
| BC025787.1 | alkB, alkylation repair homolog 1 (*E. coli*) (ALKBH1) |
| NM_153207.2 | AE binding protein 2 (AEBP2) |
| BC031799.1 | Acyl-coenzyme A thioesterase 4 |
| NM_152340.1 | hypothetical protein FLJ39075 (FLJ39075) |
| NM_201443.1 | TEA domain family member 4 (TEAD4), transcript variant 3 |
| NM_032641.1 | splA/ryanodine receptor domain and SOCS box containing 2 (SPSB2) |
| BC038976.1 | Rho GTPase-activating protein 15 |
| NM_016062.1 | family with sequence similarity 96, member B (FAM96B) |
| BC021906.1 | formin-like 1 (FMNL1) |
| BC034784.1 | zinc finger, MYND domain containing 11 (ZMYND11) |
| NM_018105.1 | THAP domain containing, apoptosis associated protein 1 (THAP1), transcript variant 1 |
| NM_144659.1 | t-complex 10 (mouse)-like (TCP10L) |
| BC009368.2 | SWI/SNF related, matrix associated, actin dependent regulator of chromatin, subfamily d, member 1 (SMARCD1) |
| NM_006924.3 | splicing factor, arginine/serine-rich 1 (splicing factor 2, alternate splicing factor) (SFRS1), transcript variant 1 |
| NM_133491.2 | spermidine/spermine N1-acetyltransferase 2 (SAT2) |
| NM_000341.2 | solute carrier family 3 (cystine, dibasic and neutral amino acid transporters, activator of cystine, dibasic and neutral amino acid transport), member 1 (SLC3A1) |
| NM_173080.1 | small proline-rich protein 4 (SPRR4) |
| BC020221.1 | SH3 and cysteine rich domain (STAC) |
| NM_016940.1 | RWD domain containing 2B (RWDD2B) |
| NM_000978.2 | ribosomal protein L23 (RPL23) |
| BC004876.1 | Protein MCM10 homolog |
| BC001108.1 | PIH1 domain-containing protein 1 |
| BC001304.1 | piccolo (presynaptic cytomatrix protein) (PCLO) |
| NM_005793.3 | non-metastatic cells 6, protein expressed in (nucleoside-diphosphate kinase) (NME6) |
| NM_201403.1 | MOB1, Mps One Binder kinase activator-like 2C (yeast) (MOBKL2C), transcript variant 2 |
| NM_021107.1 | mitochondrial ribosomal protein S12 (MRPS12), nuclear gene encoding mitochondrial protein, transcript variant 1 |

TABLE 1*-continued

| Database ID | Description |
| --- | --- |
| NM_023937.1 | mitochondrial ribosomal protein L34 (MRPL34), nuclear gene encoding mitochondrial protein |
| NM_024548.2 | leucine-rich repeats and IQ motif containing 2 (LRRIQ2) |
| NM_032563.1 | late cornified envelope 3D (LCE3D) |
| NM_022755.2 | inositol 1,3,4,5,6-pentakisphosphate 2-kinase (IPPK) |
| BC064840.1 | Histone deacetylase 7 |
| NM_003516.2 | histone cluster 2, H2aa3 (HIST2H2AA3) |
| NM_002095.1 | general transcription factor IIE, polypeptide 2, beta 34 kDa (GTF2E2) |
| BC035687.1 | flavin containing monooxygenase 5 (FMO5) |
| NM_024680.2 | E2F transcription factor 8 (E2F8) |
| NM_014473.2 | DIM1 dimethyladenosine transferase 1-like (S. cerevisiae) (DIMT1L) |
| NM_033671.1 | cyclin B3 (CCNB3), transcript variant 2 |
| NM_004143.2 | Cbp/p300-interacting transactivator 1 |
| NM_003600.1 | aurora kinase A (AURKA), transcript variant 2 |
| NM_006621.3 | S-adenosylhomocysteine hydrolase-like 1 (AHCYL1) |
| NM_198467.1 | round spermatid basic protein 1-like (RSBN1L) |
| NM_032343.1 | coiled-coil-helix-coiled-coil-helix domain containing 6 (CHCHD6) |
| BC031231.1 | serine/threonine kinase 33 (STK33) |
| NM_014047.1 | chromosome 19 open reading frame 53 (C19orf53) |
| NM_004656.2 | BRCA1 associated protein-1 (ubiquitin carboxy-terminal hydrolase) (BAP1) |
| BC006323.1 | ATP-binding cassette, sub-family B (MDR/TAP), member 7 (ABCB7) |
| BC002680.1 | thyroid hormone receptor interactor 6 (TRIP6) |
| NM_016364.2 | dual specificity phosphatase 13 (DUSP13), transcript variant 6 |
| NM_014519.2 | zinc finger protein 232 (ZNF232) |
| NM_170672.1 | RAS guanyl releasing protein 3 (calcium and DAG-regulated) (RASGRP3) |
| NM_033082.1 | Nuclear protein Hcc-1 |
| BC009350.1 | Eukaryotic translation initiation factor 2-alpha kinase 4 |
| NM_207519.1 | zeta-chain (TCR) associated protein kinase 70 kDa (ZAP70), transcript variant 2 |
| NM_017542.3 | pogo transposable element with KRAB domain (POGK) |
| NM_014268.1 | microtubule-associated protein, RP/EB family, member 2 (MAPRE2) |
| BC065030.1 | Hermansky-Pudlak syndrome 4 (HPS4) |
| BC005248.1 | eukaryotic translation initiation factor 1A, Y-linked (EIF1AY) |
| NM_022140.2 | Band 4.1-like protein 4A |
| NM_152373.2 | zinc finger protein 684 (ZNF684) |
| NM_139244.2 | syntaxin binding protein 5 (tomosyn) (STXBP5) |
| NM_006713.2 | SUB1 homolog (S. cerevisiae) (SUB1) |
| NM_003135.1 | Signal recognition particle 19 kDa protein |
| NM_004697.3 | PRP4 pre-mRNA processing factor 4 homolog (yeast) (PRPF4) |
| BC029424.1 | Probable glutathione peroxidase 8 |
| NM_016059.3 | peptidylprolyl isomerase (cyclophilin)-like 1 (PPIL1) |
| BC008741.1 | PDZ and LIM domain 5 (PDLIM5) |
| NM_032349.1 | nudix (nucleoside diphosphate linked moiety X)-type motif 16-like 1 (NUDT16L1) |
| NM_145109.1 | mitogen-activated protein kinase kinase 3 (MAP2K3), transcript variant B |
| BC001419.1 | mitochondrial trans-2-enoyl-CoA reductase (MECR) |
| BC098112.1 | Histone H2B type 1-N |
| NM_002136.1 | heterogeneous nuclear ribonucleoprotein A1 (HNRNPA1), transcript variant 1 |
| BC000251.1 | Glycogen synthase kinase-3 beta |
| NM_007278.1 | GABA(A) receptor-associated protein (GABARAP) |
| BC021561.1 | FACT complex subunit SPT16 |
| BC033159.1 | DnaJ (Hsp40) homolog, subfamily C, member 8 (DNAJC8) |
| BC014949.1 | DEXH (Asp-Glu-X-His) box polypeptide 58 (DHX58) |
| NM_152727.4 | copine II (CPNE2) |
| NM_001001709.1 | chromosome 9 open reading frame 170 (C9orf170), mRNA. |
| NM_001007246.1 | bromodomain and WD repeat domain containing 1 (BRWD1), transcript variant 3 |
| NM_181718.3 | aspartate beta-hydroxylase domain containing 1 (ASPHD1) |
| BC035582.1 | Tripartite motif-containing protein 22 |
| NM_016483.3 | PHD finger protein 7 (PHF7), transcript variant 1 |
| NM_014955.2 | KIAA0859 (KIAA0859), transcript variant 2 |
| NM_022720.5 | DiGeorge syndrome critical region gene 8 (DGCR8) |
| BC017918.1 | chromosome 9 open reading frame 19 (C9orf19) |
| NM_203425.1 | chromosome 17 open reading frame 82 (C17orf82) |
| NM_004779.4 | CCR4-NOT transcription complex, subunit 8 (CNOT8) |
| BC006811.1 | peroxisome proliferator-activated receptor gamma (PPARG) |
| BC009779.1 | outer dense fiber of sperm tails 2-like (ODF2L) |
| NM_080548.1 | Tyrosine-protein phosphatase non-receptor type 6 |
| NM_014346.1 | TBC1 domain family, member 22A (TBC1D22A) |
| NM_007107.2 | signal sequence receptor, gamma (translocon-associated protein gamma) (SSR3) |
| NM_013257.3 | serum/glucocorticoid regulated kinase family, member 3 (SGK3), transcript variant 1 |

TABLE 1*-continued

| Database ID | Description |
| --- | --- |
| NM_001022.3 | ribosomal protein S19 (RPS19) |
| NM_138453.1 | RAB3C, member RAS oncogene family (RAB3C) |
| NM_006808.2 | Protein transport protein Sec61 subunit beta |
| NM_138492.1 | PRELI domain-containing protein 2 |
| XM_379117.1 | PREDICTED: Homo sapiens hypothetical protein LOC150568 (LOC150568) |
| BC015742.1 | polymerase (DNA directed), eta (POLH) |
| BC022429.1 | Lyrm7 homolog (mouse) (LYRM7) |
| NM_022343.2 | Golgi-associated plant pathogenesis-related protein 1 |
| NM_174942.1 | GAS2-like protein 3 |
| NM_012199.2 | Eukaryotic translation initiation factor 2C 1 |
| BC053995.1 | chromosome 11 open reading frame 66 (C11orf66) |
| NM_018014.2 | B-cell CLL/lymphoma 11A (zinc finger protein) (BCL11A), transcript variant 2 |
| NM_014038.1 | basic leucine zipper and W2 domains 2 (BZW2) |
| NM_001031.4 | 40S ribosomal protein S28 |
| NM_031991.1 | polypyrimidine tract binding protein 1 (PTBP1), transcript variant 3 |
| NM_020236.2 | mitochondrial ribosomal protein L1 (MRPL1), nuclear gene encoding mitochondrial protein |
| BC017202.2 | Isovaleryl-CoA dehydrogenase, mitochondrial |
| BC014133.1 | Hsp90 co-chaperone Cdc37-like 1 |
| BC005004.1 | family with sequence similarity 64, member A (FAM64A) |
| BC029427.1 | coiled-coil domain containing 23 (CCDC23) |
| BC016312.1 | chromosome 15 open reading frame 15 (C15orf15) |
| NM_001182.2 | aldehyde dehydrogenase 7 family, member A1 (ALDH7A1) |
| NM_000461.3 | Thyroid hormone receptor beta |
| NM_005678.3 | SNRPN upstream reading frame (SNURF), transcript variant 1 |
| NM_144595.1 | SLAIN motif family, member 1 (SLAIN1), transcript variant 2 |
| NM_153819.1 | RAS guanyl releasing protein 2 (calcium and DAG-regulated) (RASGRP2), transcript variant 2, mRNA. |
| NM_001005404.3 | Protein yippee-like 2 |
| BC006376.1 | N-myristoyltransferase 2 (NMT2) |
| NM_003897.2 | immediate early response 3 (IER3) |
| BC034222.1 | HRAS-like suppressor family, member 5 (HRASLS5) |
| BC001132.1 | DEAD (Asp-Glu-Ala-Asp) box polypeptide 54 (DDX54) |
| NM_197964.1 | chromosome 7 open reading frame 55 (C7orf55) |
| NM_173541.1 | chromosome 10 open reading frame 91 (C10orf91) |
| NM_000983.3 | 60S ribosomal protein L22 |
| BC014037.1 | Serine/threonine-protein kinase Sgk2 |
| NM_017614.3 | betaine-homocysteine methyltransferase 2 (BHMT2) |
| BC035137.1 | thyroid hormone receptor, alpha (erythroblastic leukemia viral (v-erb-a) oncogene homolog, avian) (THRA) |
| NM_003160.1 | Serine/threonine-protein kinase 13 |
| NM_006214.2 | phytanoyl-CoA 2-hydroxylase (PHYH), transcript variant 1 |
| BC006177.1 | Metastasis-associated protein MTA1 |
| PHC0076 | interleukin 7 (IL7) |
| NM_021639.2 | GC-rich promoter binding protein 1-like 1 (GPBP1L1) |
| NM_001312.2 | cysteine-rich protein 2 (CRIP2) |
| BC029524.1 | Coiled-coil domain-containing protein 46 |
| NM_007189.1 | ATP-binding cassette, sub-family F (GCN20), member 2 (ABCF2), nuclear gene encoding mitochondrial protein, transcript variant 1 |
| BC022251.1 | zinc finger, AN1-type domain 1 (ZFAND1) |
| BC054030.1 | WD repeat domain 53 (WDR53) |
| NM_016208.1 | vacuolar protein sorting 28 homolog (S. cerevisiae) (VPS28), transcript variant 1 |
| NM_053049.2 | Urocortin-3 |
| NM_032207.1 | Uncharacterized protein C19orf44 |
| BC022344.1 | twinfilin, actin-binding protein, homolog 1 (Drosophila) (TWF1) |
| BC018950.2 | TNF receptor-associated protein 1 (TRAP1) |
| NM_003254.1 | TIMP metallopeptidase inhibitor 1 (TIMP1) |
| NM_001006667.1 | Tachykinin-3 |
| NM_006754.2 | synaptophysin-like 1 (SYPL1), transcript variant 1 |
| NM_017411.2 | survival of motor neuron 2, centromeric (SMN2), transcript variant d |
| BC016825.1 | spire homolog 1 (Drosophila) (SPIRE1) |
| BC005840.2 | Selenoprotein S (SELS) |
| BC036109.1 | SECIS binding protein 2 (SECISBP2) |
| NM_001013.2 | ribosomal protein S9 (RPS9) |
| NM_021029.3 | ribosomal protein L36a (RPL36A) |
| BC031608.1 | REST corepressor 3 (RCOR3) |
| NM_012227.1 | Putative GTP-binding protein 6 |
| NM_002732.2 | protein kinase, cAMP-dependent, catalytic, gamma (PRKACG) |
| NM_175634.1 | Protein CBFA2T1 |
| NM_002592.1 | proliferating cell nuclear antigen (PCNA), transcript variant 1 |
| NM_002235.2 | potassium voltage-gated channel, shaker-related subfamily, member 6 (KCNA6) |

TABLE 1*-continued

| Database ID | Description |
|---|---|
| NM_002631.2 | phosphogluconate dehydrogenase (PGD) |
| BC009047.1 | phosphodiesterase 9A (PDE9A) |
| NM_005037.3 | peroxisome proliferator-activated receptor gamma (PPARG), transcript variant 4 |
| NM_024057.2 | nucleoporin 37 kDa (NUP37) |
| BC014441.1 | NOL1/NOP2/Sun domain family, member 4 (NSUN4) |
| NM_018396.1 | methyltransferase like 2B (METTL2B) |
| BC038105.2 | membrane protein, palmitoylated 7 (MAGUK p55 subfamily member 7) (MPP7) |
| NM_178571.2 | hypothetical protein MGC51025 (MGC51025) |
| NM_003512.3 | Histone H2A type 1-C |
| BC021180.2 | high-mobility group box 4 (HMGB4) |
| BC008730.2 | hexokinase 1 (HK1) |
| NM_004966.2 | heterogeneous nuclear ribonucleoprotein F (HNRPF), transcript variant 3 |
| BC100766.2 | Glycoprotein Xg |
| BC000120.1 | general transcription factor IIF, polypeptide 1, 74 kDa (GTF2F1) |
| NM_005307.1 | G protein-coupled receptor kinase 4 |
| NM_017629.2 | eukaryotic translation initiation factor 2C, 4 (EIF2C4) |
| NM_018948.2 | ERBB receptor feedback inhibitor 1 (ERRFI1) |
| PV4128 | epidermal growth factor receptor (erythroblastic leukemia viral (v-erb-b) oncogene homolog, avian) (EGFR); see catalog number for detailed information on wild-type or point mutant status |
| BC027612.2 | EP300-interacting inhibitor of differentiation 3 |
| NM_004092.2 | Enoyl-CoA hydratase, mitochondrial |
| NM_004016.1 | dystrophin (muscular dystrophy, Duchenne and Becker types) (DMD), transcript variant Dp71b |
| NM_006651.2 | complexin 1 (CPLX1) |
| NM_022101.1 | chromosome X open reading frame 56 (CXorf56) |
| BC005955.1 | chromosome 8 open reading frame 53 (C8orf53) |
| NM_023080.1 | chromosome 8 open reading frame 33 (C8orf33) |
| NM_174891.2 | chromosome 14 open reading frame 79 (C14orf79) |
| BC001968.1 | Cell division protein kinase 9 |
| NM_001892.4 | casein kinase 1, alpha 1 (CSNK1A1), transcript variant 2 |
| BC032124.1 | Bromodomain containing 3 (BRD3) |
| NM_001204.3 | Bone morphogenetic protein receptor type-2 |
| BC008440.1 | APAF1 interacting protein (APIP) |
| BC017594.2 | APAF1 interacting protein (APIP) |
| NM_032548.2 | ankyrin repeat and BTB (POZ) domain containing 1 (ABTB1), transcript variant 1 |
| NM_021104.1 | ribosomal protein L41 (RPL41), transcript variant 1 |
| NM_175887.2 | proline rich 15 (PRR15) |
| NM_006838.1 | methionyl aminopeptidase 2 (METAP2) |
| NM_003590.2 | cullin 3 (CUL3) |
| NM_138419.1 | Protein FAM54A |
| NM_016230.3 | cytochrome b5 reductase 4 (CYB5R4) |
| NM_148176.1 | peptidylprolyl isomerase (cyclophilin)-like 2 (PPIL2), transcript variant 3 |
| BC027937.1 | retinoic acid induced 2 (RAI2) |
| BC011668.1 | Casein kinase II subunit alpha |
| NM_182612.1 | Parkinson disease 7 domain containing 1 (PDDC1) |
| PV4202 | NIMA (never in mitosis gene a)-related kinase 1 (NEK1) |
| NM_078630.1 | male-specific lethal 3-like 1 (Drosophila) (MSL3L1), transcript variant 2 |

* Prevalent in PD serum, $p < 0.01$ by M-statistic, ordered by descending prevalence difference In another embodiment, PD diagnostic biomarkers include the protein antigens set forth in Table 2. The protein antigens in Table 2 are identified by art-accepted names as well as database identification numbers. The database identification numbers refer to the publically available protein databases of the National Center for Biotechnology Information (NCBI) which are well-known and accessible to those of ordinary skill in the art.

TABLE 2*

| Database ID | Description |
|---|---|
| NM_001544.2 | intercellular adhesion molecule 4 (Landsteiner-Wiener blood group) (ICAM4), transcript variant 1 |
| BC022098.1 | cDNA clone MGC: 31944 IMAGE: 4878869, complete cds |
| NM_006628.4 | cyclic AMP phosphoprotein, 19 kD (ARPP-19) |

TABLE 2*-continued

| Database ID | Description |
|---|---|
| NM_024754.2 | pentatricopeptide repeat domain 2 (PTCD2) |
| BC051695.1 | FERM domain containing 8 (FRMD8) |
| BC016380.1 | cDNA clone MGC: 27376 IMAGE: 4688477, complete cds |
| NM_032855.1 | hematopoietic SH2 domain containing (HSH2D) |
| BC094687.1 | Elongation factor 1-alpha 1 |
| BC015833.1 | cDNA clone MGC: 27152 IMAGE: 4691630, complete cds |
| BC005858.1 | fibronectin 1 (FN1) |
| BC030984.1 | cDNA clone MGC: 32654 IMAGE: 4701898, complete cds |
| NM_002305.2 | lectin, galactoside-binding, soluble, 1 (galectin 1) (LGALS1) |

TABLE 2*-continued

| Database ID | Description |
|---|---|
| NM_000939.1 | Proopiomelanocortin (adrenocorticotropin/beta-lipotropin/alpha-melanocyte stimulating hormone/beta-melanocyte stimulating hormone/beta-endorphin) (POMC), transcript variant 2 |
| BC003551.1 | transglutaminase 2 (C polypeptide, protein-glutamine-gamma-glutamyltransferase) (TGM2) |
| PHR5001 | Recombinant human CTLA-4/Fc |
| NM_003141.2 | tripartite motif-containing 21 (TRIM21) |
| NM_001167.2 | baculoviral IAP repeat-containing 4 (BIRC4) |
| NM_006790.1 | myotilin (MYOT) |
| BC030813.1 | cDNA clone MGC: 22645 IMAGE: 4700961, complete cds |
| BC032451.1 | cDNA clone MGC: 40426 IMAGE: 5178085, complete cds |
| BC015818.1 | lectin, galactoside-binding, soluble, 8 (galectin 8) (LGALS8) |
| BC026030.1 | zinc finger protein 239 (ZNF239) |
| NM_207430.1 | FLJ46266 protein (FLJ46266), mRNA. |
| BC027951.1 | Cas scaffolding protein family member 4 |
| BC000103.1 | NCK adaptor protein 2 (NCK2) |
| NM_002648.1 | pim-1 oncogene (PIM1) |
| PHC1244 | chemokine (C-C motif) ligand 19 (CCL19) |
| NM_001001794.1 | family with sequence similarity 116, member B (FAM116B) |
| BC036365.1 | PH domain-containing protein C10orf81 |
| BC036923.1 | chromosome 9 open reading frame 150 (C9orf150) |
| NM_025104.2 | Protein DBF4 homolog B |
| NM_016207.2 | cleavage and polyadenylation specific factor 3, 73 kDa (CPSF3) |
| BC032825.2 | SH3-domain GRB2-like 2 (SH3GL2) |
| NM_004853.1 | syntaxin 8 (STX8) |
| BC006423.1 | Serine/threonine-protein kinase 6 |
| BC010074.2 | FUS interacting protein (serine/arginine-rich) 1 (FUSIP1) |
| BC036723.1 | Fc fragment of IgG, low affinity IIIa, receptor (CD16a) (FCGR3A) |
| NM_020168.3 | p21(CDKN1A)-activated kinase 6 (PAK6) |
| NM_002135.3 | nuclear receptor subfamily 4, group A, member 1 (NR4A1), transcript variant 1 |
| NM_024668.1 | ankyrin repeat and KH domain containing 1 (ANKHD1), transcript variant 3 |
| BC054021.1 | pterin-4 alpha-carbinolamine dehydratase/dimerization cofactor of hepatocyte nuclear factor 1 alpha (TCF1) 2 (PCBD2) |
| XM_379194.1 | PREDICTED: Homo sapiens hypothetical LOC401068 (LOC401068) |
| BC001935.1 | cyclin-dependent kinase inhibitor 1A (p21, Cip1) (CDKN1A) |
| NM_021130.1 | peptidylprolyl isomerase A (cyclophilin A) (PPIA) |
| NM_002307.1 | lectin, galactoside-binding, soluble, 7 (galectin 7) (LGALS7) |
| NM_014321.2 | origin recognition complex, subunit 6 like (yeast) (ORC6L) |
| BC005332.1 | cDNA clone MGC: 12418 IMAGE: 3934658, complete cds |
| BC000633.1 | Dual specificity protein kinase TTK |
| NM_002813.4 | proteasome (prosome, macropain) 26S subunit, non-ATPase, 9 (PSMD9) |
| BC027865.1 | chromosome 11 open reading frame 16 (C11orf16) |
| BC019015.2 | mediator complex subunit 29 (MED29) |
| NM_153750.1 | chromosome 21 open reading frame 81 (C21orf81) |
| NM_003503.2 | Cell division cycle 7-related protein kinase |
| NM_003177.3 | spleen tyrosine kinase (SYK) |
| NM_006145.1 | DnaJ (Hsp40) homolog, subfamily B, member 1 (DNAJB1) |
| BC035143.1 | Tigger transposable element-derived protein 1 |
| NM_012424.2 | Ribosomal protein S6 kinase delta-1 |
| BC009108.1 | cDNA clone IMAGE: 3451214 (MCM10) |
| BC006105.1 | chromosome 6 open reading frame 134 (C6orf134) |
| NM_021032.2 | fibroblast growth factor 12 (FGF12), transcript variant 1 |
| NM_152772.1 | T-complex protein 11-like protein 2 |
| NM_013242.1 | chromosome 16 open reading frame 80 (C16orf80) |
| NM_024033.1 | chromosome 7 open reading frame 49 (C7orf49) |
| BC063500.1 | Tigger transposable element-derived protein 1 |
| XM_378879.2 | PREDICTED: Homo sapiens hypothetical LOC400763 (LOC400763) |
| NM_152597.3 | Fibrous sheath-interacting protein 1 |
| NM_014288.2 | Centromere protein R |
| PV3851 | MAP/microtubule affinity-regulating kinase 4 |
| NM_005340.1 | histidine triad nucleotide binding protein 1 (HINT1) |
| NM_014747.2 | regulating synaptic membrane exocytosis 3 (RIMS3) |
| NM_012280.1 | FtsJ homolog 1 (E. coli) (FTSJ1), transcript variant 1 |
| NM_001009880.1 | chromosome 22 open reading frame 9 (C22orf9), transcript variant 2 |
| NM_053006.1 | testis-specific serine kinase 2 (TSSK2) |
| NM_018328.1 | methyl-CpG binding domain protein 5 (MBD5) |
| NM_016829.1 | 8-oxoguanine DNA glycosylase (OGG1), nuclear gene encoding mitochondrial protein, transcript variant 2e |
| NM_019058.1 | DNA-damage-inducible transcript 4 protein |
| NM_024979.2 | Guanine nucleotide exchange factor DBS |
| BC000896.1 | RAB10, member RAS oncogene family (RAB10) |
| NM_003160.1 | Serine/threonine-protein kinase 13 |
| NM_053005.2 | HCCA2 protein (HCCA2) |
| NM_145174.1 | DnaJ (Hsp40) homolog, subfamily B, member 7 (DNAJB7) |
| NM_016203.2 | protein kinase, AMP-activated, gamma 2 non-catalytic subunit (PRKAG2), transcript variant a, mRNA. |
| NM_080659.1 | chromosome 11 open reading frame 52 (C11orf52) |
| BC001280.1 | Serine/threonine-protein kinase 6 |
| BC000442.1 | Serine/threonine-protein kinase 12 |
| NM_199188.1 | La ribonucleoprotein domain family, member 4 (LARP4), transcript variant 1 |
| NM_003942.1 | Ribosomal protein S6 kinase alpha-4 |
| BC047722.1 | hypothetical protein MGC52110 (MGC52110) |
| NM_014891.1 | PDGFA associated protein 1 (PDAP1) |
| BC022378.1 | zinc finger with KRAB and SCAN domains 1 (ZKSCAN1) |
| NM_032321.1 | hypothetical protein MGC13057 (MGC13057), transcript variant 4 |
| BC050718.1 | Polymerase (DNA directed) kappa (POLK) |
| NM_145050.1 | coiled-coil domain containing 26 (CCDC26) |
| BC014928.1 | MYC-induced nuclear antigen |
| NM_005922.1 | Mitogen-activated protein kinase kinase kinase 4 |
| BC015732.1 | histidine triad nucleotide binding protein 3 (HINT3) |

*Prevalent in PD serum, p < 0.0001, Prevalence difference >40%, ordered by descending prevalence difference In another embodiment, PD diagnostic biomarkers include the protein antigens set forth in Table 3. In another embodiment, the PD diagnostic biomarkers include pentatricopeptide repeat domain 2 (PTCD2). In another embodiment, the PD diagnostic biomarkers include FERM domain containing 8 (FRMD8). The protein antigens in Table 3 are identified by art-accepted names as well as database identification numbers. The database identification numbers refer to the publically available protein databases of the National Center for Biotechnology Information (NCBI) which are well-known and accessible to those of ordinary skill in the art.

TABLE 3

| Database ID | Description |
|---|---|
| NM_001544.2 | intercellular adhesion molecule 4 (Landsteiner-Wiener blood group) (ICAM4), transcript variant 1 |
| NM_024754.2 | pentatricopeptide repeat domain 2 (PTCD2) |
| BC051695.1 | FERM domain containing 8 (FRMD8) |
| PHR5001 | Recombinant human CTLA-4/Fc |
| NM_006790.1 | myotilin (MYOT) |
| NM_032855.1 | hematopoietic SH2 domain containing (HSH2D) |
| BC005858.1 | fibronectin 1 (FN1) |
| NM_003141.2 | tripartite motif-containing 21 (TRIM21) |
| BC094687.1 | Elongation factor 1-alpha 1 |
| BC027617.1 | poly(A) binding protein, cytoplasmic 3 (PABPC3) |

In another embodiment, the PD diagnostic biomarkers are diagnostic for early-stage PD and include the protein antigens set forth in Table 4. The protein antigens in Table 4 are identified by art-accepted names as well as database identification numbers. The database identification numbers refer to the publically available protein databases of the National Center for Biotechnology Information (NCBI) which are well-known and accessible to those of ordinary skill in the art.

TABLE 4*

| Database ID | Description |
| --- | --- |
| BC014452.1 | cDNA clone IMAGE: 4903661, complete cds |
| PHC1244 | chemokine (C-C motif) ligand 19 (CCL19) |
| NM_002147.2 | homeobox B5 (HOXB5) |
| BC018929.1 | pleckstrin homology-like domain, family A, member 1 (PHLDA1) |
| NM_014925.2 | R3H domain-containing protein 2 |
| BC028565.1 | Protein Daple |
| NM_144659.1 | t-complex 10 (mouse)-like (TCP10L) |
| NM_002690.1 | Polymerase (DNA directed), beta (POLB) |
| NM_005898.4 | cell cycle associated protein 1 (CAPRIN1), transcript variant 1 |
| NM_022140.2 | Band 4.1-like protein 4A |
| NM_194290.1 | cDNA F1142001 fis, clone SPLEN2029912 (LOC153684 protein) [Source: UniProtKB/TrEMBL; Acc: Q6ZVW3] |
| BC060767.1 | centaurin, beta 2 (CENTB2) |
| BC026039.1 | mitochondrial GTPase 1 homolog (*S. cerevisiae*) (MTG1) |
| BC011603.1 | v-rel reticuloendotheliosis viral oncogene homolog A, nuclear factor of kappa light polypeptide gene enhancer in B-cells 3, p65 (avian) (RELA) |
| BC014667.1 | immunoglobulin heavy constant gamma 1 (G1m marker) (IGHG1) |
| | Histone-type IIA |
| BC027729.1 | tetra-peptide repeat homeobox-like (TPRXL) |
| NM_001032293.1 | zinc finger protein 207 (ZNF207), transcript variant 2 |
| NM_057749.1 | cyclin E2 (CCNE2) |
| BC010352.1 | tyrosine 3-monooxygenase/tryptophan 5-monooxygenase activation protein, beta polypeptide, mRNA (cDNA clone IMAGE: 4292790), complete cds. |
| NM_198395.1 | GTPase activating protein (SH3 domain) binding protein 1 (G3BP1), transcript variant 2 |
| NM_015122.1 | FCH domain only 1 (FCHO1) |
| NM_025041.2 | chromosome 3 open reading frame 36 (C3orf36) |
| BC022996.1 | SH3 domain-binding protein 2 |
| BC058900.1 | rabaptin, RAB GTPase binding effector protein 2 (RABEP2) |
| BC000440.1 | Cystathionine beta-synthase |
| BC060828.1 | AT rich interactive domain 3A (BRIGHT-like) (ARID3A) |
| NM_007067.3 | MYST histone acetyltransferase 2 (MYST2) |
| BC005403.1 | Uncharacterized protein C11orf57 |
| NM_014805.2 | EPM2A (laforin) interacting protein 1 (EPM2AIP1) |
| NM_173545.1 | chromosome 2 open reading frame 13 (C2orf13) |
| BC053509.1 | 5,10-methylenetetrahydrofolate reductase (NADPH) (MTHFR) |
| NM_173194.2 | Kv channel interacting protein 2 (KCNIP2), transcript variant 5 |
| PHC1475 | C-C motif chemokine 21 |
| NM_001030002.1 | Growth factor receptor-bound protein 7 |
| NM_181714.1 | Leber congenital amaurosis 5 (LCA5) |
| NM_002254.5 | kinesin family member 3C (KIF3C) |
| BC099907.1 | General transcription factor II-I |
| BC013437.1 | myocyte enhancer factor 2A (MEF2A) |
| BC005043.1 | hypothetical protein MGC31957 (MGC31957) |
| NM_004664.2 | lin-7 homolog A (*C. elegans*) (LIN7A) |
| NM_178552.2 | chromosome 22 open reading frame 33 (C22orf33) |
| NM_006832.1 | pleckstrin homology domain containing, family C (with FERM domain) member 1 (PLEKHC1) |
| BC050563.1 | hypothetical protein LOC202051 (LOC202051) |
| NM_018441.2 | peroxisomal trans-2-enoyl-CoA reductase (PECR) |
| BC009108.1 | cDNA clone IMAGE: 3451214 (MCM10) |
| NM_181712.2 | KN motif and ankyrin repeat domain-containing protein 4 |
| NM_020175.1 | dihydrouridine synthase 3-like (*S. cerevisiae*) (DUS3L) |
| NM_006607.1 | pituitary tumor-transforming 2 (PTTG2) |
| NM_004196.2 | Cyclin-dependent kinase-like 1 |
| BC017305.1 | sirtuin (silent mating type information regulation 2 homolog) 7 (*S. cerevisiae*) (SIRT7) |

TABLE 4*-continued

| Database ID | Description |
| --- | --- |
| BC011454.1 | Angiomotin like 2 (AMOTL2) |
| NM_003668.2 | mitogen-activated protein kinase-activated protein kinase 5 (MAPKAPK5), transcript variant 1 |
| NM_006148.1 | LIM and SH3 domain protein 1 |
| BC038976.1 | Rho GTPase-activating protein 15 |
| BC033758.1 | centaurin, alpha 2 (CENTA2) |
| BC025314.1 | immunoglobulin heavy constant gamma 1 (G1m marker) (IGHG1) |
| BC026101.2 | nudE nuclear distribution gene E homolog (*A. nidulans*)-like 1 (NDEL1) |
| BC012575.1 | Zinc finger CCCH domain-containing protein 7A |
| BC021211.2 | RALBP1 associated Eps domain containing 1 (REPS1) |
| NM_006674.2 | HLA complex P5 (HCP5) |
| NM_014466.2 | tektin 2 (testicular) (TEKT2) |
| NM_016319.1 | COP9 constitutive photomorphogenic homolog subunit 7A (Arabidopsis) (COPS7A) |
| NM_080664.1 | chromosome 14 open reading frame 126 (C14orf126) |
| NM_007194.2 | CHK2 checkpoint homolog (*S. pombe*) (CHEK2), transcript variant 1 |
| NM_005552.3 | Kinesin light chain 1 |
| BC071563.1 | UPF0667 protein C1orf55 |
| BC054501.1 | dynamin 2 (DNM2) |
| NM_017592.1 | Mediator of RNA polymerase II transcription subunit 29 |
| NM_007030.1 | tubulin polymerization promoting protein (TPPP) |
| BC031650.1 | Putative E3 ubiquitin-protein ligase SH3RF2 |
| NM_003910.2 | BUD31 homolog (*S. cerevisiae*) (BUD31) |
| NM_007177.1 | Protein FAM107A |
| BC014298.1 | PRKR interacting protein 1 (IL11 inducible) (PRKRIP1) |
| NM_024718.2 | chromosome 9 open reading frame 86 (C9orf86) |
| NM_001005360.1 | Dynamin-2 |
| NM_198829.1 | Ras-related C3 botulinum toxin substrate 1 |
| BC002733.2 | chromosome 1 open reading frame 77 (C1orf77) |
| BC033856.1 | La ribonucleoprotein domain family, member 1 (LARP1) |
| BC017114.1 | oligonucleotide/oligosaccharide-binding fold containing 2A (OBFC2A) |
| NM_003590.2 | cullin 3 (CUL3) |
| BC034718.1 | Erythrocyte membrane protein band 4.1-like 2 (EPB41L2) |
| NM_022650.1 | RAS p21 protein activator (GTPase activating protein) 1(RASA1), transcript variant 2 |
| BC020233.1 | cDNA clone MGC: 31936 IMAGE: 4765518, complete cds |
| NM_017819.1 | RNA (guanine-9-)-methyltransferase domain-containing protein 1, mitochondrial |
| NM_017761.2 | proline-rich nuclear receptor coactivator 2 (PNRC2) |
| BC000044.1 | Spindlin-2B |
| BC048107.1 | zinc finger protein 333 (ZNF333) |
| NM_001002755.1 | NFU1 iron-sulfur cluster scaffold homolog, mitochondrial |
| NM_032321.1 | hypothetical protein MGC13057 (MGC13057), transcript variant 4 |
| BC006091.1 | tumor suppressing subtransferable candidate 4 (TSSC4) |
| BC077077.1 | Dihydropyrimidinase-related protein 3 |
| NM_020165.2 | RAD18 homolog (*S. cerevisiae*) (RAD18) |
| BC022362.1 | cDNA clone MGC: 23888 IMAGE: 4704496, complete cds |
| BC014095.2 | v-rel reticuloendotheliosis viral oncogene homolog A, nuclear factor of kappa light polypeptide gene enhancer in B-cells 3, p65 (avian) (RELA) |
| NM_138499.2 | PWWP domain-containing protein 2B |
| NM_005522.3 | homeobox A1 (HOXA1), transcript variant 1 |
| BC062732.1 | Ig kappa chain C region |
| NM_006479.2 | RAD51 associated protein 1 (RAD51AP1) |
| NM_006590.2 | ubiquitin specific peptidase 39 (USP39) |
| BC050683.1 | zinc finger protein 410 (ZNF410) |
| BC096165.1 | Troponin I, cardiac muscle |
| BC009074.1 | chromosome 8 open reading frame 70 (C8orf70) |
| BC013795.1 | Bardet-Biedl syndrome 10 protein |
| PHC1695 | C-X-C motif chemokine 11 |
| NM_003289.3 | tropomyosin 2 (beta) (TPM2), transcript variant 1 |
| NM_199001.1 | Similar to RIKEN cDNA 2310002J15 gene (MGC59937) |
| NM_023940.1 | RAS-like, family 11, member B (RASL11B) |
| BC059947.1 | chondrosarcoma associated gene 1 (CSAG1) |

TABLE 4*-continued

| Database ID | Description |
| --- | --- |
| BC030590.1 | retinoblastoma binding protein 8 (RBBP8) |
| BC044851.1 | vacuolar protein sorting 41 homolog (*S. cerevisiae*) (VPS41) |
| NM_002055.1 | glial fibrillary acidic protein (GFAP) |
| NM_018019.1 | mediator complex subunit 9 (MED9) |
| NM_032943.2 | synaptotagmin-like 2 (SYTL2), transcript variant a |
| BC006106.1 | ribosomal protein S6 kinase, 70 kDa, polypeptide 2 (RPS6KB2) |
| NM_006443.2 | chromosome 6 open reading frame 108 (C6orf108), transcript variant 1 |
| PV3359 | Ephrin receptor A3 (EPHA3), transcript variant 1 |
| BC033195.1 | killer cell immunoglobulin-like receptor, three domains, X1 (KIR3DX1) |
| BC007852.1 | Serine/threonine-protein kinase 25 |
| NM_024299.2 | chromosome 20 open reading frame 149 (C20orf149) |
| NM_006374.2 | serine/threonine kinase 25 (STE20 homolog, yeast) (STK25) |
| NM_032370.1 | Zinc finger protein 414 |

*Prevalent in early-stage PD serum, p < 0.01 by M-statistic, ordered by descending prevalence difference In another embodiment, the PD diagnostic biomarkers are diagnostic for early-stage PD and include the protein antigens set forth in Table 5. The protein antigens in Table 5 are identified by art-accepted names as well as database identification numbers. The database identification numbers refer to the publically available protein databases of the National Center for Biotechnology Information (NCBI) which are well-known and accessible to those of ordinary skill in the art.

TABLE 5*

| Database ID | Description |
| --- | --- |
| BC014452.1 | cDNA clone IMAGE: 4903661, complete cds |
| PHC1244 | Chemokine (C-C motif) ligand 19 (CCL19) |
| NM_002147.2 | homeobox B5 (HOXB5) |
| BC018929.1 | pleckstrin homology-like domain, family A, member 1 (PHLDA1) |
| NM_014925.2 | R3H domain-containing protein 2 |
| BC028565.1 | Protein Daple |
| NM_144659.1 | t-complex 10 (mouse)-like (TCP10L) |
| NM_002690.1 | polymerase (DNA directed), beta (POLB) |
| NM_005898.4 | cell cycle associated protein 1 (CAPRIN1), transcript variant 1 |
| NM_022140.2 | Band 4.1-like protein 4A |

*Prevalentin PD serum, p < 0.005 by M-statistic, ordered by descending prevalence difference Thus in one embodiment, the present invention provides a method for detecting PD diagnostic biomarkers in a subject in need of such detection comprising obtaining an immunoglobulin-containing biological sample from the subject, and performing an assay to determine the presence or absence of one or more PD diagnostic biomarkers in the biological sample.

In another embodiment, the present invention provides a method for diagnosing PD in a subject in need of such diagnosis comprising obtaining an immunoglobulin-containing biological sample from the subject, performing an assay to determine the presence or absence of one or more PD diagnostic biomarkers in the biological sample, and diagnosing PD if one or more PD diagnostic biomarkers are present.

In a preferred embodiment, the subject is a human subject.

In a preferred embodiment of the invention, the immunoglobulin-containing biological sample is serum, plasma, whole blood, CSF, saliva, or sputum. A blood sample may be obtained by methods known in the art including venipuncture or a finger stick. CSF may be obtained by methods known in the art including a lumbar spinal tap. Serum and plasma samples may be obtained by centrifugation methods known in the art. Sputum and saliva samples may be collected by methods known in the art. The biological samples may be diluted with a suitable buffer before conducting the assay. In a preferred embodiment, the biological sample is serum, plasma, or whole blood.

Assays to determine the presence or absence of one or more PD diagnostic biomarkers in the biological sample are performed by contacting the sample with one or more antigens that are specific for an PD diagnostic biomarker under conditions that allow an immunocomplex of the antigen and the antibody to form, and detecting the presence of the immunocomplex An antigen may comprise a protein antigen of Table 1 or 4, or a polypeptide or peptide fragment thereof containing one or more epitopes recognized by the PD diagnostic biomarker, or an epitope peptidomimetic that is recognized by the PD diagnostic biomarker. Peptidomimetics include, for example, D-peptides, peptoids, and β-peptides. The antigens may be purified from natural sources, or produced recombinantly or synthetically by methods known in the art, and may be in the form of fusion proteins. The antigens may be produced in vitro using cell-free translation systems. In one preferred embodiment, the antigens are produced in a mammalian or insect expression system to ensure correct folding and function. All of these methods may be automated for high throughput production.

Assays and conditions for the detection of immunocomplexes are known to those of skill in the art. Such assays include, for example, competition assays, direct reaction assays and sandwich-type assays. The assays may be quantitative or qualitative. In one preferred embodiment, the assay utilizes a solid phase or substrate to which the antigens are directly or indirectly attached, such as a microtiter or microassay plate, slide, magnetic bead, non-magnetic bead, column, matrix, membrane, or sheet, and may be composed of a synthetic material such as polystyrene, polyvinyl chloride, polyamide, or other synthetic polymers, natural polymers such as cellulose, derivatized natural polymers such as cellulose acetate or nitrocellulose, and glass, for example glass fibers. The substrate preferably comprises a plurality of individually addressable antigens immobilized on the surface. The individually addressable antigens are preferably immobilized on the surface to form an array. The substrates may be used in suitable shapes, such as films, sheets, or plates, or may be coated onto or bonded or laminated to appropriate inert carriers, such as paper, glass, plastic films, or fabrics. In a preferred embodiment, the substrate is a slide or a bead.

Methods for attaching the antigens to the support or substrate are known in the art and include covalent and noncovalent interactions. For example, diffusion of applied proteins into a porous surface such a hydrogel allows noncovalent binding of unmodified protein within hydrogel structures. Covalent coupling methods provide a stable linkage and may be applied to a range of proteins. Biological capture methods utilising a tag (e.g., hexahistidine/Ni-NTA or biotin/avidin) on the protein and a partner reagent immobilized on the surface of the substrate provide a stable linkage and bind the protein specifically and in reproducible orientation.

In one preferred embodiment, the antigens are coated or spotted onto the support or substrate such as chemically derivatized glass, or a glass plate coated with a protein binding agent such as, but not limited to, nitrocellulose.

In one preferred embodiment the antigens are provided in the form of an array, and preferably a microarray. Protein microarrays are known in the art and reviewed for example by Hall et al. (2007) *Mech Ageing Dev* 128:161-167 and Stoevesandt et al (2009) *Expert Rev Proteomics* 6:145-157, the disclosures of which are incorporated herein by reference. Microarrays may be prepared by immobilizing purified antigens on a substrate such as a treated microscope slide using a contact spotter or a non-contact microarrayer. Microarrays may also be produced through in situ cell-free synthesis directly from corresponding DNA arrays.

Suitable methods for external production and purification of antigens to be spotted on arrays include expression in bacteria, as disclosed for example by Venkataram et al. (2008) *Biochemistry* 47:6590-6601, in yeast, as disclosed for example by Li et al. (2007) *Appl Biochem Biotechnol.* 142:105-124, in insect cells, as disclosed for example by Altman et al. (1999) *Glycoconj J* 16:109-123, and in mammalian cells, as disclosed for example by Spampinato et al. (2007) *Curr Drug Targets* 8:137-146.

Suitable methods for in situ ("on-chip") protein production are disclosed, for example, by Ramachandran et al. (2006) *Methods Mol. Biol* 2328:1-14 and He et al. (2008) *Curr. Opin Biotechnol* 19:4-9.

Other methods by which proteins are simultaneously expressed and immobilized in parallel on an array surface are also known in the art and may be used in accordance with the present invention. For example, in the Protein In Situ Arrays (PISA) method (He et al. (2001) *Nucleic Acids Res* 29:e73), proteins are made directly from DNA, either in solution or immobilized, and become attached to the array surface as they are made through recognition of a tag sequence. The proteins are expressed in parallel in vitro utilizing a cell free system, commonly rabbit reticulocyte or *E. coli* S30, to perform coupled transcription and translation. In this method, protein expression is performed on a surface which is precoated with an immobilizing agent capable of binding to the tag. Thus after each protein is translated, it becomes fixed simultaneously and specifically to the adjacent surface, while the other materials can subsequently be washed away. Microarrays are produced directly onto glass slides, either by mixing the DNA with the cell free lysate system before spotting or by a multiple spotting technique (MIST) in which DNA is spotted first followed by the expression system.

In the system known as Nucleic Acid Programmable Protein Array (NAPPA) (Ramachandran et al. (2004) *Science* 305:86-90), transcription and translation from an immobilized (as opposed to a solution) DNA template allow conversion of DNA arrays to protein arrays. In this method, biotinylated cDNA plasmids encoding the proteins as GST fusions are printed onto an avidin-coated slide, together with an anti-GST antibody acting as the capture entity. The cDNA array is then covered with rabbit reticulocyte lysate to express the proteins, which become trapped by the antibody adjacent to each DNA spot, the proteins thereby becoming immobilized with the same layout as the cDNA. This technology generates a protein array in which the immobilized proteins are present together with DNA and a capture agent.

Another suitable method for generating a protein array is the DNA Array to Protein Array (DAPA) method. This method for in situ protein arraying uses an immobilized DNA array as the template to generate 'pure' protein arrays on a separate surface from the DNA, and also can produce multiple copies of a protein array from the same DNA template (He et al. (2008) *Nature Methods*, 5:175-7). Cell-free protein synthesis is performed in a membrane held between two surfaces (e.g., glass slides), one of which is arrayed with DNA molecules while the other surface carries a specific reagent to capture the translated proteins. Individual, tagged proteins are synthesized in parallel from the arrayed DNA, diffuse across the gap and are subsequently immobilized through interaction with the tag-capturing reagent on the opposite surface to form a protein array. Discrete spots which accurately reflect the DNA in position and quantity are produced. Replicate copies of the protein array can be obtained by reuse of the DNA.

Array fabrication methods include robotic contact printing, ink-jetting, piezoelectric spotting and photolithography. For example, purified antigens of the invention that are produced and purified externally may be spotted onto a microarray substrate using a flexible protein microarray inkjet printing system (e.g., ArrayJet, Roslin, Scotland, UK) to provide high quality protein microarray production. The precise rows and columns of antigens may be converted to detectable spots denoting both the presence and amount of diagnostic biomarkers that have been bound.

The production of the microarrays is preferably performed with commercially available printing buffers designed to maintain the three-dimensional shape of the antigens. In one preferred embodiment, the substrate for the microarray is a nitrocellulose-coated glass slide.

The assays are performed by methods known in the art in which the one or more antigens are contacted with the biological sample under conditions that allow the formation of an immunocomplex of an antigen and an antibody, and detecting the immunocomplex. The presence and amount of the immunocomplex may be detected by methods known in the art, including label-based and label-free detection. For example, label-based detection methods include addition of a secondary antibody that is coupled to an indicator reagent comprising a signal generating compound. The secondary antibody may be an anti-human IgG antibody. Indicator reagents include chromogenic agents, catalysts such as enzyme conjugates, fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors and magnetic particles. Examples of enzyme conjugates include alkaline phosphatase, horseradish peroxidase and beta-galactosidase. Methods of label-free detection include surface plasmon resonance, carbon nanotubes and nanowires, and interferometry. Label-based and label-free detection methods are known in the art and disclosed, for example, by Hall et al. (2007) and by Ray et al. (2010) *Proteomics* 10:731-748. Detection may be accomplished by scanning methods known in the art and appropriate for the label used, and associated analytical software.

In one preferred embodiment of the present invention, fluorescence labeling and detection methods are used to detect the immunocomplexes. Commericially available slide scanners (e.g. the Genepix 4000B slide scanner (Molecular Devices, Inc.) with associated analytical software may be used. In one preferred embodiment, the immunocomplex is probed with fluorescent-labeled (e.g., Alexa-Fluor (Invitrogen)) anti-human antibody and the intensity of fluorescence at each protein spot is measured using a microarray scanner. Commercially available software (e.g. GenePix Pro 5.0 software (Axon instruments)) may be used to extract the net median pixel intensities for individual features from the digital images produced by the scanner. Data may be normalized by comparing median values of multiple identical control spots in different regions of the same array.

Detection of diagnostic immunocomplexes is indicative of the presence of PD diagnostic biomarkers in the biological sample, and thus a positive diagnosis of PD.

In another embodiment, the present invention provides a method of generating a patient-specific PD diagnostic biomarker profile comprising obtaining a serum-containing biological sample from a patient, performing an assay to determine the presence or absence of PD diagnostic biomarkers in the biological sample, and generating a patient-specific PD diagnostic biomarker profile of the PD diagnostic biomarkers present in the sample. The assay is performed as described hereinabove.

The results of the assay provide an PD diagnostic biomarker profile for the patient that is useful to diagnose PD and optimize a treatment regimen for PD.

In another embodiment, the present invention provides a method of identifying a subject at risk for developing PD comprising obtaining an immunoglobulin-containing biological sample from the subject, performing an assay to determine the presence or absence of one or more PD diagnostic biomarkers in the biological sample, and identifying the subject as at risk for developing PD if one or more of the PD diagnostic biomarkers is present. The assay is performed as described herein above.

In yet another embodiment, the present invention provides a substrate on which one or more antigens that are specific for a PD diagnostic biomarker are immobilized. The present invention also provides, in another embodiment, a microarray comprising a substrate on which one or more antigens that are specifically bound by an PD diagnostic biomarker are immobilized. The substrates and microarrays may be made as described hereinabove and are useful for creating PD diagnostic biomarker profiles and for the diagnosis of PD. An antigen may comprise a protein antigen of Table 1 or 4, or a polypeptide or peptide fragment thereof containing one or more epitopes recognized by the PD diagnostic biomarker, or an epitope peptidomimetic that is recognized by the PD diagnostic biomarker. Peptidomimetics include, for example, D-peptides, peptoids, and β-peptides. The substrate and microarrays may contain, as the antigen, at least one of the protein antigens of Table 1 or 4 or fragments thereof containing one or more epitopes recognized by the PD diagnostic biomarker.

In another embodiment, the substrate and microarrays may contain, as the antigen, at least one of the protein antigens of Table 2, 3 or 5, or or a polypeptide or peptide fragment thereof containing one or more epitopes recognized by the PD diagnostic biomarker, or an epitope peptidomimetic that is recognized by the PD diagnostic biomarker. Peptidomimetics include, for example, D-peptides, peptoids, and β-peptides. In another preferred embodiment of the present invention, the substrate and microarrays contain at least two, or at least three, or at least four, or at least five, or at least six, or at least seven, or at least eight, or at least nine, or all of the protein antigens of Table 2, 3 or 5 or polypeptides or peptide fragments thereof containing one or more epitopes recognized by the PD diagnostic biomarker, or epitope peptidomimetics that are recognized by the PD diagnostic biomarkers of Table 2, 3 or 5. In another preferred embodiment of the present invention, the substrate and microarrays contain PTCD2 or polypeptides or peptide fragments thereof containing one or more epitopes recognized by the PTCD2 diagnostic biomarker, or epitope peptidomimetics that are recognized by the PTCD2 diagnostic biomarker. In another preferred embodiment of the present invention, the substrate and microarrays contain FRMD8 or polypeptides or peptide fragments thereof containing one or more epitopes recognized by the FRMD8 diagnostic biomarker, or epitope peptidomimetics that are recognized by the FRMD8 diagnostic biomarker.

In a further embodiment, the present invention provides a kit for detecting PD-specific antibodies in a sample. A kit comprises one or more antigens that are specific for a PD diagnostic biomarker and means for determining binding of the antigen to a PD diagnostic biomarker in the sample. The kit may also comprise packaging material comprising a label that indicates that the one or more antigens of the kit can be used for the identification of PD. Other components such as buffers, controls, detection reagents, and the like known to those of ordinary skill in art may be included in such the kits. The kits are useful for detecting PD diagnostic biomarkers and for diagnosing PD.

The following examples serve to further illustrate the present invention.

Example 1

Materials and Methods

Human Brain Tissue.

Human brain tissue from six control (non-PD) individuals was obtained from the Cooperative Human Tissue Network (Philadelphia, Pa.).

Human Serum Samples.

Twenty-nine Parkinson's disease (PD) serum samples, 50 AD samples, and 40 control samples were obtained from Analytical Biological Systems, Inc. (Wilmington, Del.). Thirty breast cancer (BC) serum samples and 10 multiple sclerosis (MS) serum samples were obtained from Asterand, Inc. (Detroit, Mich.). In an attempt to develop a diagnostic with broad application to all PD patients at all stages of the disease, the PD serum pool contained samples from early, progressive and late stage PD subjects. All samples were handled by standard procedures and stored at −80° C. Diagnosis of PD was based on a clinical evaluation based on Gelb criteria (Gelb et al. (1999) Archives of Neurology 56:33-39). Demographic characteristics of the study population are shown in Table 6.

TABLE 6

Demographics of Serum Donors

| Group | n | Age Mean | Age Range | Sex (% male) |
| --- | --- | --- | --- | --- |
| Parkinson's disease | 29 | 74.0 | 53-88 | 55% |
| Alzheimer's disease | 50 | 78.5 | 61-97 | 40% |
| Multiple Sclerosis | 10 | 46.0 | 27-59 | 30% |
| Breast Cancer | 30 | 46.7 | 32-54 | 0% |
| Controls | 40 | 40.4 | 19-86 | 82% |
| Older Control | 20 | 57.7 | 51-86 | 100% |
| Younger Control | 20 | 24.7 | 19-30 | 65% |

Human Protein Microarrays.

To identify autoantibodies in human sera, Invitrogen's ProtoArray v5.0 Human Protein Microarrays (Cat. No. PAH0525020, Invitrogen, Carlsbad, Calif., USA), each containing 9,486 unique human protein antigens, were used. All proteins were expressed as GST fusion proteins in insect cells, purified under native conditions, and spotted in duplicate onto nitrocellulose-coated glass slides. All arrays were probed and scanned according to the manufacturer's instructions using commercially prepared reagents. Briefly, microarray slides were blocked (Blocking Buffer, Cat. No.

PA055, Invitrogen) and then incubated with serum samples, diluted 1:500 in washing buffer. After washing, the arrays were probed with anti-human IgG (H+L) conjugated to AlexaFluor 647 (Cat. No. A-21445, Invitrogen). Arrays were then washed, dried, and immediately scanned with a GenePix 4000B Fluorescence Scanner (Molecular Devices, Sunnyvale, Calif., USA).

Dot Blot Analyses.

One µl volumes of purified, recombinant human FRMD8 (0.2 µg/µl) protein (Cat. No. TP307879, OriGene Technologies, Inc., Rockville, Md., USA), were manually pipetted onto nitrocellulose membranes. The protein was blocked in a 5% non-fat milk PBS-Tween solution for one hour at room temperature (RT), and then probed with human serum samples diluted 1:2000 for one hour at RT. All sera were identical to those used to probe the human protein microarrays. The dot blots were probed with an antihuman IgG (H+L) HRP conjugate antibody (Cat. No. 31410, Thermo Fisher Scientific Inc., Pittsburgh, Pa., USA) for one hour at RT, incubated with ECL reagent (Cat. No. 34096, Thermo Fisher Scientific Inc., Pittsburgh, Pa., USA) for one minute, and then exposed to X-ray films. The films were scanned to grayscale picture files and quantified using Image J software. After normalization, comparison on dot blot assay was done with a two tailed T-test.

Microarray Data Analyses.

The fluorescence data for each microarray were acquired by Genepix Pro analysis software after scanning, and then synced with Invitrogen's lot-specific Genepix Array List (GAL) files. The resulting Genepix Results (GPR) files were then imported into Invitrogen's Prospector 5.2 for analysis. All data were MIAME compliant and the raw data were deposited in a MIAME compliant database (GEO). The "group characterization" and "two-group comparison" features in the IRBP Toolbox allowed for M-statistical analysis of autoantibody expression. Sorting detectable autoantibodies by difference of prevalence between PD and control groups in descending order, the top 10 were selected as potential diagnostic biomarkers.

The selected biomarkers were re-verified as significant by Predictive Analysis for Microarrays (PAM)—an independent algorithm relying on nearest shrunken centroid analysis to identify proteins acting as significant class-differentiators. The predictive classification accuracy of the identified biomarkers was tested with Random Forest (RF) using the default settings, another significance algorithm run as an R package (v 2.12.1). In RF, partitioning trees were built by successively splitting the samples according to a measure of statistical impurity at a given node until terminal nodes were as homogenous as possible. Classification accuracy for a given set of diagnostic biomarkers was reported in a confusion matrix and misclassification as an Out-Of-Bag (OOB) error score.

Immunohistochemical Detection of Target Antigens.

Formalin-fixed human cerebral cortex and substantia nigra were processed for routine paraffin embedding and sectioning according to established protocols. Immunohistochemistry was carried out as described by Birkmayer et al. (1961) *Wiener klinische Wochenschrift* 73:787-788. Following antigen retrieval, endogenous peroxidase was quenched by treating sections with 0.3% $H_2O_2$ for 10 min. Sections were incubated in blocking serum and then treated with primary antibody for 1 hour at room temperature. After rinsing in phosphate buffer, secondary antibody was applied for 30 minutes. After another washing, sections were treated with the avidin-biotin-peroxidase complex (Cat. PK-6100, Vector Laboratories, CA) and then visualized with diaminobenzidine (DAB) substrate (Cat. K3468, Dako, Calif.). For substantia nigra tissue sections, alkaline phosphatase conjugated secondary antibody together with nitro blue tetrazolium (NBT) diformazan substrate (Cat. B 1911, Sigma, Mo.) was used to detect the expression of FRMD8 in melanin pigmented substantia nigra neurons. The sources of antibodies were: Rabbit polyclonal anti-FRMD8 IgG, Santa Cruz, Calif., Cat. SC-138944; anti-MAP2, anti-GFAP, anti-HLA-DR (Millipore, Temecula, Calif.); biotin conjugated secondary anti-rabbit IgG, Vector Laboratories, CA, Cat. PK-6101; alkaline phosphatase conjugated secondary anti-rabbit IgG, Sigma, Mo., Cat. A9919. Controls consisted of brain sections treated with omission of the primary antibody. Specimens were examined and photographed with a Nikon FXA microscope, and digital images were recorded using a Nikon DXM1200F digital camera.

Example 2

Identification of Biomarkers Diagnostic for PD

Selection of Autoantibody Biomarkers for PD Diagnosis.

A total of 69 human serum samples (29 PD and 40 controls; Table 4) were assigned to either a Training Set (15 PD, 20 control) or Testing Set (14 PD, 20 control), each containing equal proportions of early-, progressive-, and late-stage PD samples as well as older and younger controls. To identify potential diagnostic autoantibodies for PD, human protein microarrays, each containing 9,486 native antigens, were probed with Training Set sera and data were analyzed as described in above. Prospector analysis software determined that 780 autoantibodies had a significantly higher prevalence in the PD group than in the control group ($p<0.01$) and thus represent PD biomarkers. The 10 autoantibody biomarkers that demonstrated the largest difference in group prevalence between PD and controls were selected to serve as diagnostic indicators (Table 7). As an independent verification of the 10 biomarkers selected, data were re-evaluated with Predictive Analysis for Microarrays (PAM) (Tibshirani et al. (2002) *Proc. Natl. Acad. Sci. USA* 99:6567-6572). PAM confirmed that the 10 biomarkers originally selected by Prospector were among the most significant classifiers of PD and controls.

TABLE 7

Identity and Significance of 10 PD vs. Control Diagnostic Biomarkers

| Database ID | Description | Prevalence in PD | Prevalence in Controls | p |
|---|---|---|---|---|
| NM_001544.2 | intercellular adhesion molecule 4 (Landsteiner-Wiener blood group) (ICAM4), transcript variant 1 | 93.55% | 2.38% | 1.73E−18 |
| NM_024754.2 | pentatricopeptide repeat domain 2 (PTCD2) | 90.32% | 7.14% | 9.40E−13 |

TABLE 7-continued

Identity and Significance of 10 PD vs. Control Diagnostic Biomarkers

| Database ID | Description | Prevalence in PD | Prevalence in Controls | p |
|---|---|---|---|---|
| BC051695.1 | FERM domain containing 8 (FRMD8) | 87.10% | 4.76% | 1.31E−14 |
| PHR5001 | Recombinant human CTLA-4/Fc | 87.10% | 14.29% | 6.14E−11 |
| NM_006790.1 | myotilin (MYOT) | 90.32% | 21.43% | 5.66E−10 |
| NM_032855.1 | hematopoietic SH2 domain containing (HSH2D) | 87.10% | 7.14% | 1.71E−13 |
| BC005858.1 | fibronectin 1 (FN1) | 90.32% | 14.29% | 7.39E−08 |
| NM_003141.2 | tripartite motif-containing 21 (TRIM21) | 80.65% | 9.52% | 1.07E−10 |
| BC094687.1 | Elongation factor 1-alpha 1 | 87.10% | 7.14% | 3.03E−10 |
| BC027617.1 | poly(A) binding protein, cytoplasmic 3 (PABPC3) | 74.19% | 11.91% | 0.000805 |

Verification of Biomarkers Via Training and Testing Set Analyses.

To assess the Training and Testing set classification accuracies of the selected biomarkers, Random Forest (RF) was used (Breiman et al. (2001) *Machine Learning* 45:5-32). RF is a statistical algorithm that creates voting classes of decision-making trees to evaluate the significance of each marker and classify samples. Using the 10 biomarkers to "diagnose" the Training Set (n=35; PD and 20 control), RF had an overall accuracy of greater than 97.1% [Out-of-Bag (OOB) Error 2.9%, a positive predictive value (PPV) of 100%, and a negative predictive value (NPV) of 95.2%]. When the same 10 biomarkers were used to classify the Testing Set sera (n=34; 14 PD and 20 control), which played no part in the biomarker selection process, RF distinguished PD samples from controls with a similar accuracy (prediction error of 2.9%, PPV of 100.0%, and NPV of 95.2%). When the 10 autoantibody biomarkers were used to classify all PD and control samples simultaneously (n=69; 29 PD, 40 control) in RF, they did so with a 93.1% sensitivity and 100% specificity.

Differentiation of PD from Other Diseases.

Using the 10 selected autoantibody markers, PD samples were correctly differentiated from controls with a high and consistent accuracy (Table 6). To test for disease specificity, the ability to differentiate PD from other non-neurological and neurological diseases was assessed. To accomplish this, the 10 selected biomarkers were used to differentiate 30 breast cancer serum samples from the 29 PD samples. RF reported an OOB Error of 3.39% (PPV and NPV of 93.5% and 100%, respectively). These results are similar to those of the PD versus control trials described above and demonstrate that there is no diagnostic bias toward disease in general. To verify biomarker specificity against another central nervous system disorder, Multiple Sclerosis (MS) sera was used as a neurologically diseased control. Results show that the 10 PD autoantibody biomarkers can distinguish PD and MS samples with 100% accuracy (Table 8). These results indicate that these biomarkers provide a specific and reliable PD diagnostic.

TABLE 8

Diagnostic Accuracies of Selected Biomarkers

| | PD (n = 29) vs. | | | | | |
|---|---|---|---|---|---|---|
| | All Controls n = 40 | Older Control n = 20 | Younger Control n = 20 | AD* n = 50 | Breast Cancer n = 30 | MS n = 10 |
| Sensitivity % | 93.1 | 96.6 | 96.6 | 82.8 | 100.0 | 100.0 |
| Specificity % | 100.0 | 100.0 | 100.0 | 88.0 | 93.3 | 100.0 |
| PPV % | 100.0 | 100.0 | 100.0 | 80.0 | 93.5 | 100.0 |
| NPV % | 95.2 | 95.2 | 95.2 | 89.8 | 100.0 | 100.0 |

*The biomarkers for this study are in Table 4 of Nagele et al. (2011) *PLoS One* 6(8): e23112; all others are the biomarkers identified in Table 7.

Dot Blot Confirmation of Potential Biomarkers.

To further validate the differential expression of autoantibodies detected with human protein microarrays, a comparative dot-blot analysis using commercially-obtained, purified, native proteins was performed. One of the most potent differentiating antigens identified, FERM domain containing 8 protein (FRMD8), was selected and its reactivity to PD and control sera was verified. The native protein was spotted onto nitrocellulose membrane and probed with identical sera to those used on the microarrays. Results from both PD and control sera showed strong agreement in the relative intensities of the FRMD8 immunoreactions between protein microarrays and dot blots. The majority of PD sera (n=29) reacted intensely to purified FRMD8 protein, while most control sera (n=36) showed either a weak or no reaction. Dot blot quantification using Image J revealed that the average PD serum reactivity to FRMD8 protein was 6.7 times higher than control serum (p<0.05). Thus, the dot blot assays independently confirmed the results obtained from protein microarrays: i.e., anti-FRMD8 antibodies are more predominant in PD sera than in control sera, and so are useful as diagnostic biomarkers of PD.

Immunohistochemical Confirmation of Target Antigen Expression in the Substantia Nigra.

The immunogenic production of PD-specific serum autoantibodies would indicate that the antigen targets of these autoantibodies are normally expressed in the specific brain regions characteristically affected by PD, such as the substantia nigra. To test for target protein expression in the human substantia nigra, immunohistochemistry and commercially prepared antibodies to FRMD8, the antigen target of one of the selected autoantibody biomarkers were used. Examination of this brain region from three subjects confirmed abundant FRMD8 immunopositive staining. Intense linear and punctuate labeling of the pars compacta interstitium indicated FRMD8 localization within axons, while most cytoplasmic regions of the neuronal cell bodies and all glial cells were generally immunonegative (Fig. 4B). Given the eventual cortical degradation witnessed in PD patients and that FRMD8 autoantibodies are also seen as differentially expressed in AD sera (Nagele et al. (2011) *PLoS One* 6(8):e23112), normal human cerebral cortex tissue was also examined. Pyramidal neurons were strongly and selectively immunopositive for FRMD8. These results clearly show that FRMD8, the antigen of an identified PD autoantibody biomarker, is expressed in regions affected by the pathology: the substantia nigra and cerebral cortex.

Example 3

Identification of Biomarkers Diagnostic for Early Stage PD

Using the human protein microarrays and analyses described hereinabove in Example 1, autoantibodies were identified in early-stage (prior to any drug treatment) PD blood samples provided by the Michael J. Fox Foundation. Autoantibodies for the biomarkers in Table 4 below had a significantly higher prevalence in the PD group than in the control group (p<0.01) and thus the biomarkers in Table 4 represent early-stage PD biomarkers. Specifically, using data from 64 early-stage PD blood samples and 62 controls, early-stage PD was detected with over 90% accuracy using this biomarker set.

TABLE 4*

| Database ID | Description |
| --- | --- |
| BC014452.1 | cDNA clone IMAGE: 4903661, complete cds |
| PHC1244 | chemokine (C-C motif) ligand 19 (CCL19) |
| NM_002147.2 | homeobox B5 (HOXB5) |
| BC018929.1 | pleckstrin homology-like domain, family A, member 1 (PHLDA1) |
| NM_014925.1 | R3H domain-containing protein 2 |
| BC028565.1 | Protein Daple |
| NM_144659.1 | t-complex 10 (mouse)-like (TCP10L) |
| NM_002690.1 | polymerase (DNA directed), beta (POLB) |
| NM_005898.4 | cell cycle associated protein 1 (CAPRIN1), transcript variant 1 |
| NM_022140.2 | Band 4.1-like protein 4A |
| NM_194290.1 | cDNA FLJ42001 fis, clone SPLEN2029912 (LOC153684 protein) [Source: UniProtKB/TrEMBL; Acc: Q6ZVW3] |
| BC060767.1 | centaurin, beta 2 (CENTB2) |
| BC026039.1 | mitochondrial GTPase 1 homolog (*S. cerevisiae*) (MTG1) |
| BC011603.1 | v-rel reticuloendotheliosis viral oncogene homolog A, nuclear factor of kappa light polypeptide gene enhancer in B-cells 3, p65 (avian) (RELA) |
| BC014667.1 | immunoglobulin heavy constant gamma 1 (G1m marker) (IGHG1) |
| | Histone-type IIA |
| BC027729.1 | tetra-peptide repeat homeobox-like (TPRXL) |
| NM_001032293.1 | zinc finger protein 207 (ZNF207), transcript variant 2 |
| NM_057749.3 | cyclin E2 (CCNE2) |
| BC010352.1 | tyrosine 3-monooxygenase/tryptophan 5-monooxygenase activation protein, beta polypeptide, mRNA (cDNA clone IMAGE: 4292790), complete cds. |
| NM_198395.1 | GTPase activating protein (SH3 domain) binding protein 1 (G3BP1), transcript variant 2 |
| NM_015122.1 | FCH domain only 1 (FCHO1) |
| NM_025041.2 | chromosome 3 open reading frame 36 (C3orf36) |
| BC022996.1 | SH3 domain-binding protein 2 |
| BC058900.1 | rabaptin, RAB GTPase binding effector protein 2 (RABEP2) |
| BC000440.1 | Cystathionine beta-synthase |

TABLE 4*-continued

| Database ID | Description |
| --- | --- |
| BC060828.1 | AT rich interactive domain 3A (BRIGHT-like) (ARID3A) |
| NM_007067.3 | MYST histone acetyltransferase 2 (MYST2) |
| BC005403.1 | Uncharacterized protein C11orf57 |
| NM_014805.2 | EPM2A (laforin) interacting protein 1 (EPM2AIP1) |
| NM_173545.1 | chromosome 2 open reading frame 13 (C2orf13) |
| BC053509.1 | 5,10-methylenetetrahydrofolate reductase (NADPH) (MTHFR) |
| NM_173194.2 | Kv channel interacting protein 2 (KCNIP2), transcript variant 5 |
| PHC1475 | C-C motif chemokine 21 |
| NM_001030002.1 | Growth factor receptor-bound protein 7 |
| NM_181714.1 | Leber congenital amaurosis 5 (LCA5) |
| NM_002254.5 | kinesin family member 3C (KIF3C) |
| BC099907.1 | General transcription factor II-I |
| BC013437.1 | myocyte enhancer factor 2A (MEF2A) |
| BC005043.1 | hypothetical protein MGC31957 (MGC31957) |
| NM_004664.2 | lin-7 homolog A (*C. elegans*) (LIN7A) |
| NM_178552.2 | chromosome 22 open reading frame 33 (C22orf33) |
| NM_006832.1 | pleckstrin homology domain containing, family C (with FERM domain) member 1 (PLEKHC1) |
| BC050563.1 | hypothetical protein LOC202051 (LOC202051) |
| NM_018441.2 | peroxisomal trans-2-enoyl-CoA reductase (PECR) |
| BC009108.1 | cDNA clone IMAGE:3451214 (MCM10) |
| NM_181712.2 | KN motif and ankyrin repeat domain-containing protein 4 |
| NM_020175.1 | dihydrouridine synthase 3-like (*S. cerevisiae*) (DUS3L) |
| NM_006607.1 | pituitary tumor-transforming 2 (PTTG2) |
| NM_004196.2 | Cyclin-dependent kinase-like 1 |
| BC017305.1 | sirtuin (silent mating type information regulation 2 homolog) 7 (*S. cerevisiae*) (SIRT7) |
| BC011454.1 | angiomotin like 2 (AMOTL2) |
| NM_003668.2 | mitogen-activated protein kinase-activated protein kinase 5 (MAPKAPK5), transcript variant 1 |
| NM_006148.1 | LIM and SH3 domain protein 1 |
| BC038976.1 | Rho GTPase-activating protein 15 |
| BC033758.1 | centaurin, alpha 2 (CENTA2) |
| BC025314.1 | immunoglobulin heavy constant gamma 1 (G1m marker) (IGHG1) |
| BC026101.2 | nudE nuclear distribution gene E homolog (*A. nidulans*)-like 1 (NDEL1) |
| BC012575.1 | Zinc finger CCCH domain-containing protein 7A |
| BC021211.2 | RALBP1 associated Eps domain containing 1 (REPS1) |
| NM_006674.2 | HLA complex P5 (HCP5) |
| NM_014466.2 | tektin 1 (testicular) (TEKT2) |
| NM_016319.1 | COP9 constitutive photomorphogenic homolog subunit 7A (*Arabidopsis*) (COPS7A) |
| NM_080664.1 | chromosome 14 open reading frame 126 (C14orf126) |
| NM_007194.2 | CHK2 checkpoint homolog (*S. pombe*) (CHEK2), transcript variant 1 |
| NM_005552.3 | Kinesin light chain 1 |
| BC071563.1 | UPF0667 protein C1orf55 |
| BC054501.1 | dynamin 2 (DNM2) |
| NM_017592.1 | Mediator of RNA polymerase II transcription subunit 29 |
| NM_007030.1 | tubulin polymerization promoting protein (TPPP) |
| BC031650.1 | Putative E3 ubiquitin-protein ligase SH3RF2 |
| NM_003910.2 | BUD31 homolog (*S. cerevisiae*) (BUD31) |
| NM_007177.1 | Protein FAM107A |
| BC014298.1 | PRKR interacting protein 1 (IL11 inducible) (PRKRIP1) |
| NM_024718.2 | chromosome 9 open reading frame 86 (C9orf86) |
| NM_001005360.1 | Dynamin-2 |
| NM_198829.1 | Ras-related C3 botulinum toxin substrate 1 |
| BC002733.2 | chromosome 1 open reading frame 77 (C1orf77) |
| BC033856.1 | La ribonucleoprotein domain family, member 1 (LARP1) |
| BC017114.1 | oligonucleotide/oligosaccharide-binding fold containing 2A (OBFC2A) |
| NM_003590.2 | cullin 3 (CUL3) |
| BC034718.1 | erythrocyte membrane protein band 4.1-like 2 (EPB41L2) |
| NM_022650.1 | RAS p21 protein activator (GTPase activating protein) 1(RASA1), transcript variant 2 |
| BC020233.1 | cDNA clone MGC: 31936 IMAGE: 4765518, complete cds |
| NM_017819.1 | RNA (guanine-9-)-methyltransferase domain-containing protein 1, mitochondrial |

TABLE 4*-continued

| Database ID | Description |
|---|---|
| NM_017761.2 | proline-rich nuclear receptor coactivator 2 (PNRC2) |
| BC000044.1 | Spindlin-2B |
| BC048107.1 | zinc finger protein 333 (ZNF333) |
| NM_001002755.1 | NFU1 iron-sulfur cluster scaffold homolog, mitochondrial |
| NM_032321.1 | hypothetical protein MGC13057 (MGC13057), transcript variant 4 |
| BC006091.1 | tumor suppressing subtransferable candidate 4 (TSSC4) |
| BC077077.1 | Dihydropyrimidinase-related protein 3 |
| NM_020165.2 | RAD18 homolog (S. cerevisiae) (RAD18) |
| BC022362.1 | cDNA clone MGC: 23888 IMAGE: 4704496, complete cds |
| BC014095.2 | v-rel reticuloendotheliosis viral oncogene homolog A, nuclear factor of kappa light polypeptide gene enhancer in B-cells 3, p65 (avian) (RELA) |
| NM_138499.2 | PWWP domain-containing protein 2B |
| NM_005522.3 | homeobox A1 (HOXA1), transcript variant 1 |
| BC062732.1 | Ig kappa chain C region |
| NM_006479.2 | RAD51 associated protein 1 (RAD51AP1) |
| NM_006590.2 | ubiquitin specific peptidase 39 (USP39) |
| BC050683.1 | zinc finger protein 410 (ZNF410) |
| BC096165.1 | Troponin I, cardiac muscle |
| BC009074.1 | chromosome 8 open reading frame 70 (C8orf70) |
| BC013795.1 | Bardet-Biedl syndrome 10 protein |
| PHC1695 | C-X-C motif chemokine 11 |
| NM_003289.3 | tropomyosin 2 (beta) (TPM2), transcript variant 1 |
| NM_199001.1 | Similar to RIKEN cDNA 2310002J15 gene (MGC59937) |
| NM_023940.1 | RAS-like, family 11, member B (RASL11B) |
| BC059947.1 | chondrosarcoma associated gene 1 (CSAG1) |
| BC030590.1 | retinoblastoma binding protein 8 (RBBP8) |
| BC044851.1 | vacuolar protein sorting 41 homolog (S. cerevisiae) (VPS41) |
| NM_002055.1 | glial fibrillary acidic protein (GFAP) |
| NM_018019.1 | mediator complex subunit 9 (MED9) |
| NM_032943.2 | synaptotagmin-like 2 (SYTL2), transcript variant a |
| BC006106.1 | ribosomal protein S6 kinase, 70 kDa, polypeptide 2 (RPS6KB2) |
| NM_006443.2 | chromosome 6 open reading frame 108 (C6orf108), transcript variant 1 |
| PV3359 | Ephrin receptor A3 (EPHA3), transcript variant 1 |
| BC033195.1 | killer cell immunoglobulin-like receptor, three domains, X1 (KIR3DX1) |
| BC007852.1 | Serine/threonine-protein kinase 25 |
| NM_024299.2 | chromosome 20 open reading frame 149 (C20orf149) |
| NM_006374.2 | serine/threonine kinase 25 (STE20 homolog, yeast) (STK25) |
| NM_032370.1 | Zinc finger protein 414 |

*Prevalent in early-stage PD serum, p < 0.01 by M-statistic, ordered by descending prevalence difference All references cited herein are incorporated by reference herein in their entireties.

I claim:

1. A method for detecting the presence of autoantibodies in a subject in need thereof comprising:
   a) obtaining an immunoglobulin-containing biological sample from the subject, and
   b) performing an assay on said biological sample to detect binding between at least two autoantibodies and at least two antigens selected from the group consisting of intercellular adhesion molecule 4 (ICAM4), elongation factor 1-alpha 1, tripartite motif-containing 21 (TRIM21), and hematopoietic SH2 domain containing (HSH2D),
   wherein the binding is detected through the presence of immunocomplexes formed between said at least two autoantibodies and said at least two antigens.

2. The method of claim 1 wherein one of the antigens is ICAM4 or a fragment thereof.

3. The method of claim 1 wherein one of the antigens is elongation factor 1-alpha 1.

4. The method of claim 1 wherein the immunoglobulin-containing sample is serum, plasma, or whole blood.

5. The method of claim 1 wherein the at least two antigens are attached to a substrate.

6. The method of claim 1 wherein the at least two antigens are in the form of an array.

7. The method of claim 6 wherein the array is a microarray.

8. The method of claim 5 wherein the substrate is a nitrocellulose-coated glass slide.

9. The method of claim 1 wherein the at least two antigens further comprises an additional antigen selected from the group consisting of interleukin-20 (IL20), C-C motif chemokine 19 (CCL19), and serine-threonine-protein kinase (MARK1).

10. The method of claim 1 wherein the at least two antigens further comprises at least two additional antigens selected from the group consisting of interleukin-20 (IL20), C-C motif chemokine 19 (CCL19), and serine-threonine-protein kinase (MARK1).

11. The method of claim 1 wherein the at least two antigens further comprise each of interleukin-20 (IL20), C-C motif chemokine 19 (CCL19), and serine-threonine-protein kinase (MARK1).

12. The method of claim 1 wherein step b) performing an assay on said biological sample comprises detecting binding between at least three autoantibodies and at least three antigens selected from the group consisting of intercellular adhesion molecule 4 (ICAM4), elongation factor 1-alpha 1, tripartite motif-containing 21 (TRIM21), and hematopoietic SH2 domain containing (HSH2D), wherein the binding is detected through the presence of immunocomplexes formed between said at least three autoantibodies and said at least three antigens.

13. The method of claim 12 wherein the at least three antigens further comprise at least one additional antigen biomarker selected from the group consisting of interleukin-20 (IL20), C-C motif chemokine 19 (CCL19), and serine/threonine-protein kinase (MARK1).

14. The method of claim 12 wherein the at least three antigens further comprise at least two additional antigens selected from the group consisting of interleukin-20 (IL20), C-C motif chemokine 19 (CCL19), and serine-threonine-protein kinase (MARK1).

15. The method of claim 12 wherein the at least three antigens further comprise each of interleukin-20 (IL20), C-C motif chemokine 19 (CCL19), and serine-threonine-protein kinase (MARK1).

16. The method of claim 1 wherein step b) performing an assay on said biological sample comprises detecting binding between at least four autoantibodies and the following four antigens; intercellular adhesion molecule 4 (ICAM4), elongation factor 1-alpha 1, tripartite motif containing 21 (TRIM21), and hematopoietic SH2 domain containing (HSH2D), wherein the binding is detected through the presence of immunocomplexes formed between said at least four autoantibodies and said four antigens.

17. The method of claim 16 wherein at least one additional antigen selected from the group consisting of interleukin-20 (IL-20), C-C motif chemokine 19 (CCL19), and serine/threonine-protein kinase (MARK1) is determine to be present in said biological sample.

18. The method of claim 17 wherein at least two of said additional antigens are present in said biological sample.

19. The method of claim 17 wherein all three of said additional antigens are present in said biological sample.

20. The method of claim 1, wherein the presence of immunocomplexes formed between said at least two autoantibodies and said at least two antigens is detected by adding a secondary antibody that binds to said immunocomplexes, the secondary antibody being coupled to an indicator reagent comprising a signal generating compound.

21. The method of claim 20, wherein said secondary antibody is an anti-human IgG antibody.

22. The method of claim 1, wherein the patient in need thereof is suffering from PD or is at risk of developing PD.

* * * * *